US008815560B2

(12) United States Patent
Nedwin et al.

(10) Patent No.: US 8,815,560 B2
(45) Date of Patent: Aug. 26, 2014

(54) ALPHA-AMYLASE BLEND FOR STARCH PROCESSING AND METHOD OF USE THEREOF

(71) Applicant: Danisco US Inc., Palo Alto, CA (US)

(72) Inventors: Glenn E. Nedwin, Davis, CA (US);
Vivek Sharma, North Liberty, IA (US);
Jayarama K. Shetty, Pleasanton, CA (US)

(73) Assignee: Danisco US Inc., Palo Alto, CA (US)

( * ) Notice: Subject to any disclaimer, the term of this patent is extended or adjusted under 35 U.S.C. 154(b) by 0 days.

(21) Appl. No.: 14/014,046

(22) Filed: Aug. 29, 2013

(65) Prior Publication Data

US 2014/0087429 A1 Mar. 27, 2014

Related U.S. Application Data

(62) Division of application No. 13/389,797, filed as application No. PCT/US2010/043369 on Jul. 27, 2010, now Pat. No. 8,545,907.

(60) Provisional application No. 61/232,276, filed on Aug. 7, 2009.

(51) Int. Cl.
*C12N 9/32* (2006.01)
*C07K 1/00* (2006.01)

(52) U.S. Cl.
USPC ............................................ 435/204; 530/350

(58) Field of Classification Search
USPC .......................................... 435/204; 530/350
See application file for complete search history.

(56) References Cited

U.S. PATENT DOCUMENTS

| 4,536,477 A | 8/1985 | Katkocin et al. |
| 4,560,651 A | 12/1985 | Nielsen et al. |
| RE32,153 E | 5/1986 | Tamura et al. |
| 4,587,215 A | 5/1986 | Hirsh |
| 4,717,662 A | 1/1988 | Montgomery et al. |
| 5,055,403 A | 10/1991 | Tomimura |
| 5,180,669 A | 1/1993 | Antrim |
| 5,281,526 A | 1/1994 | Good et al. |
| 5,736,375 A | 4/1998 | Deweer et al. |
| 5,817,498 A | 10/1998 | Deweer et al. |
| 5,958,739 A | 9/1999 | Mitchinson et al. |
| 6,309,871 B1 | 10/2001 | Outtrup et al. |
| 6,475,762 B1 | 11/2002 | Stafford et al. |
| 7,202,057 B2 | 4/2007 | Lovenberg et al. |
| 7,273,740 B2 | 9/2007 | Callen et al. |
| 7,323,336 B2 | 1/2008 | Callen et al. |
| 7,399,623 B2 | 7/2008 | Miller et al. |
| 7,407,677 B2 | 8/2008 | Callen et al. |
| 7,413,879 B2 | 8/2008 | Dunn-Coleman et al. |
| 8,058,033 B2 | 11/2011 | Aehle et al. |
| 8,206,966 B2 | 6/2012 | Cascao-Pereira et al. |
| 2003/0138786 A1 | 7/2003 | Callen et al. |
| 2004/0258829 A1* | 12/2004 | Zheng et al. ............... 426/615 |
| 2008/0083406 A1 | 4/2008 | Svendsen et al. |
| 2008/0153733 A1 | 6/2008 | Andersen |
| 2008/0160573 A1 | 7/2008 | Ferrari et al. |
| 2008/0220476 A1 | 9/2008 | Tang et al. |
| 2008/0220498 A1 | 9/2008 | Cervin et al. |
| 2009/0238923 A1 | 9/2009 | Shaw et al. |

FOREIGN PATENT DOCUMENTS

| EP | 0063909 | 11/1982 |
| EP | 238023 | 9/1987 |
| EP | 2042548 (A1) | 4/2009 |
| WO | WO8402921 | 8/1984 |
| WO | WO8601831 | 3/1986 |
| WO | WO9004136 | 4/1990 |
| WO | WO9117243 | 11/1991 |
| WO | WO9200381 | 1/1992 |
| WO | WO9535382 | 12/1995 |
| WO | WO9623874 | 8/1996 |
| WO | WO9639528 | 12/1996 |
| WO | WO9741213 | 11/1997 |
| WO | WO9901545 | 1/1999 |
| WO | WO9902702 | 1/1999 |
| WO | WO9919467 | 4/1999 |
| WO | WO9928448 | 6/1999 |
| WO | WO9949740 | 10/1999 |
| WO | WO0004136 | 1/2000 |
| WO | WO0147956 | 7/2001 |
| WO | WO0151620 | 7/2001 |
| WO | WO02068589 | 9/2002 |
| WO | WO2004091544 | 10/2004 |
| WO | WO2006043178 | 4/2006 |
| WO | WO2008045489 | 4/2008 |
| WO | WO2008153805 | 12/2008 |

OTHER PUBLICATIONS

Altschul, et al., "Gapped BLAST and PSI-BLAST: a new generation of protein database search programs", Nucleic Acids Res, (1997), 25:3389-402.

(Continued)

*Primary Examiner* — Maryam Monshipouri
(74) *Attorney, Agent, or Firm* — Danisco US Inc.

(57) ABSTRACT

The present disclosure relates to an enzyme blend comprising a low pH, thermostable alpha-amylase and a *Bacillus licheniformis* alpha-amylase. The blend can include at least about 1.0 Liquefon Unit (LU) of the *B. licheniformis* alpha-amylase for every 5.0 Modified Wohlgemuth Unit (MWU) of the low pH, thermostable alpha-amylase. The enzyme blend described is suitable for starch liquefaction and saccharification, ethanol production, and/or sweetener production, among other things. Also provided herein is a method of processing a starch by liquefying the starch with the low pH, thermostable alpha-amylase and the *Bacillus licheniformis* alpha-amylase, simultaneously or sequentially.

35 Claims, 1 Drawing Sheet

(56) References Cited

OTHER PUBLICATIONS

Boel, et al., "Glucoamylases G1 and G2 from *Aspergillus niger* are synthesized from two different but closely related mRNAs", EMBO J, (1984), 3:1097-102.

Chen, et al., "Identification and elimination by site-directed mutagenesis of thermolabile aspartyl bonds in *Aspergillus* awamori glucoamylase", Protein Eng, (1995), 8:575-82.

Chen, et al., "Substitution of asparagine residues in *Aspergillus* awamori glucoamylase by site-directed mutagenesis to eliminate N-glycosylation and inactivation by deamidation", Biochem J, (1994) 301:275-81.

Cleland, et al., "Baume-Dry Substance Tables for Starch Suspensions", Ind Eng Chem anal Ed, (1943), 15:334-6.

Engelen, et al., "Simple and rapid determination of phytase activity", J AOAC Int, (1994), 77:760-4.

Fierobe, et al., "Mutational modulation of substrate bond-type specificity and thermostability of glucoamylase from *Aspergillus* awamori by replacement with short homologue active site sequences and thiol/disulfide engineering", Biochemistry, (1996), 35:8696-704.

Fogarty, et al., "Starch-degrading enzymes of microbial origin", Progress in Industrial Microbiology, (1979), 15:112-115.

Hata, et al., "The glucoamylase cDNA from *Aspergillus oryzae*: its cloning, nucleotide sequence, and expression in *Saccharomyces cerevisiae*", Agric Biol Chem, (1991), 55:941-9.

Kaneko, et al., "Characterization of acid-stable glucose isomerase from *Streptomyces* sp., and development of single-step processes for high-fructose corn sweetener (HFCS) production", Biosci Biotechnol Biochem, (2000), 64:940-7.

Kelly, et al., "Molecular genetic analysis of the pullulanase B gene of *Bacillus acidopullulyticus*", FEMS Microbiol Lett, (1994), 115:97-105.

Li, et al., "Effect of introducing proline residues on the stability of *Aspergillus* awamomori", Protein Eng, (1997), 10:1199-204.

Maarel (van der), et al., "Properties and applications of starch-converting enzymes of the alpha-amylase family", J Biotechnol, (2002) 94:137-55.

MacGregor, et al., "Relationship of sequence and structure to specificity in the alpha-amylase family of enzymes", Biochim Biophys Acta, (2001), 1546:1-20.

Nelson, et al., "A Photometric Adaptation of the Somogyi Method for the Determination of Glucose", J Biol Chem, (1944), 153:375-80.

Pearson, et al., "Improved tools for biological sequence comparison", Proc Natl Acad Sci, (1988), 85:2444-8.

Richardson, et al., "A novel, high performance enzyme for starch liquefaction. Discovery and optimization of a low pH, thermostable alpha-amylase", J Biol Chem, (2002), 277:26501-7.

Russell et al., "Rational modification of enzyme catalysis by engineering surface charge", Nature, (1987), 328:496-500.

Sheridan, et al., "It came from beneath the sea", Nat Biotechnol, (2005), 23:1199-201.

Somogyi, et al., "A new reagent for the determination of sugars", J Biol Chem, (1945), 160:61-68.

\* cited by examiner

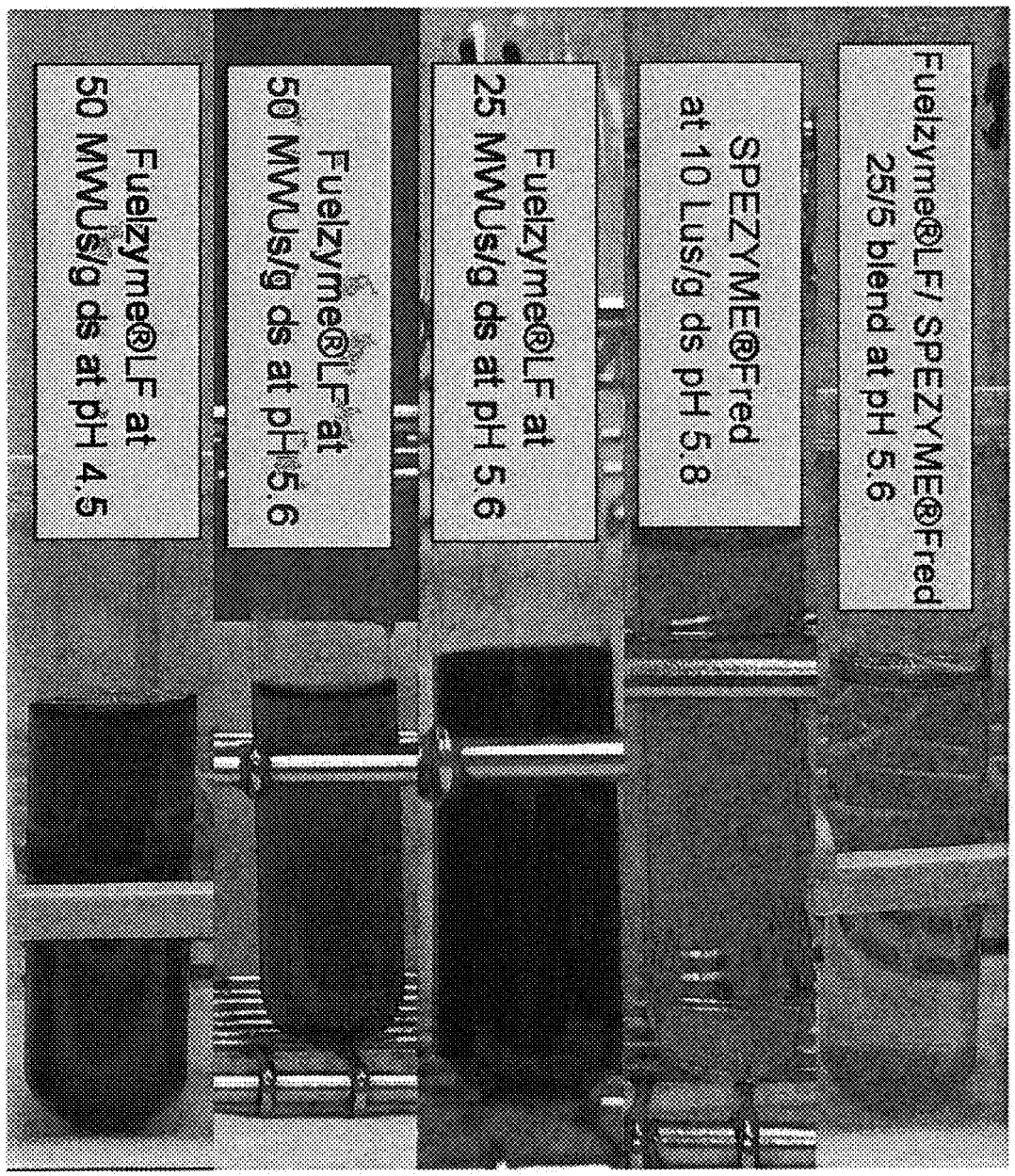

ALPHA-AMYLASE BLEND FOR STARCH PROCESSING AND METHOD OF USE THEREOF

CROSS REFERENCE TO RELATED APPLICATIONS

The present application is a Divisional of U.S. application Ser. No. 13/389,797, filed Jul. 27, 2010, now U.S. Pat. No. 8,545,907, which is a 371 National Phase of PCT/US2010/043369, filed Mar. 20, 2012, which claims priority to U.S. Provisional Application Ser. No. 61/232,276 filed on Aug. 7, 2009, which is hereby incorporated by reference in its entirety.

SEQUENCE LISTING

The sequence listing submitted via EFS, in compliance with 37 C.F.R. §1.52(e), is incorporated herein by reference. The sequence listing text file submitted via EFS contains the file "31172-WO_ST25.txt", created on Nov. 22, 2013, which is 20,480 bytes in size.

FIELD OF THE INVENTION

Described herein is a method of processing a starch by contacting a low pH, thermostable alpha-amylase and a *Bacillus licheniformis* alpha-amylase to a starch substrate to liquefy the starch. The enzymes may be added as a blend or in sequence. The enzyme blend described herein is suitable for starch liquefaction and saccharification, ethanol production, and/or sweetener production, among other things. Also described is a method of processing starch by using the low pH, thermostable alpha-amylase and the *Bacillus licheniformis* alpha-amylase to liquefy the starch.

BACKGROUND

Starches from grain, cereals, and tubers, e.g., cornstarch, are widely used in the industrial manufacture of products such as sugar syrups and biofuels. For example, high fructose corn syrup (HFCS) is a processed form of corn glucose syrup having high fructose content and a sweetness comparable to sucrose, making HFCS useful as a sugar substitute in soft drinks and other processed foods. HFCS production currently represents a billion dollar industry. Similarly, the production of ethanol from starches is a rapidly expanding industry.

Syrups and biofuels can be produced from starch by an enzymatic process that catalyzes the breakdown of starch into glucose. This enzymatic process typically involves a sequence of enzyme-catalyzed reactions:

(1) Liquefaction: Alpha-amylases (EC 3.2.1.1) first catalyze the degradation of a starch suspension, which may contain 30-40% w/w dry solids (ds), to maltodextrans.

Alpha-amylases are endohydrolases that catalyze the random cleavage of internal α-1,4-D-glucosidic bonds. Because liquefaction typically is conducted at high temperatures, e.g., 90-100° C., thermostable alpha-amylases, such as alpha-amylases from *Bacillus* sp., are preferred for this step. Alpha-amylases currently used for this step, e.g., alpha-amylases from *B. licheniformis*, *B. amyloliquefaciens*, and *Geobacillus stearothermophilus* (AmyS), do not produce significant amounts of glucose. Instead, the resulting liquefact has a low dextrose equivalent (DE), containing maltose and sugars with high degrees of polymerization (DPn).

(2) Saccharification: Glucoamylases catalyze the hydrolysis of alpha-1,4-glucosidic linkages of maltodextrins formed after liquefaction from non-reducing ends, releasing D-glucose. Saccharification produces high glucose syrup. Debranching enzymes, such as pullulanases, can aid saccharification.

(3) Further Processing: A branch point in the process occurs after the production of a glucose-rich syrup. If the final desired product is a biofuel, yeast can ferment the glucose-rich syrup to ethanol. On the other hand, if the final desired product is a fructose-rich syrup, glucose isomerase can catalyze the conversion of the glucose-rich syrup to fructose.

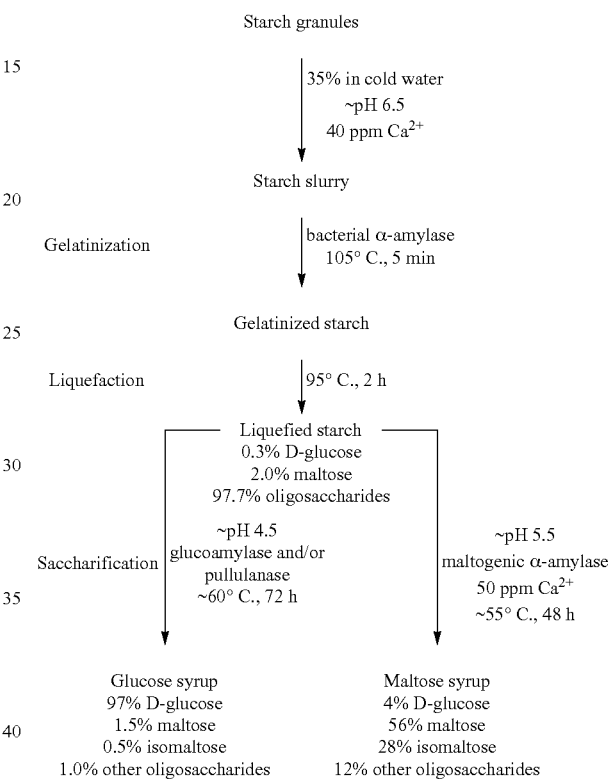

Alpha-amylases are isolated from a wide variety of bacterial, fungal, plant, and animal sources. Many industrially important alpha-amylases are isolated from *Bacillus* sp., in part because of the generally high capacity of *Bacillus* to secrete amylases into the growth medium. In addition, *Bacillus* alpha-amylase variants with altered while more desirable properties are obtained through genetic engineering. Furthermore, there is a need for blends of alpha-amylases, or variants thereof, which can capitalize on the best properties of at least two alpha-amylases of different origins.

The Fuelzyme®-LF alpha-amylase (SEQ ID NO: 2)(Verenium Corp.) is an engineered alpha-amylase obtained through DNA shuffling of three parental enzymes. See Richardson et al., *J. Biol. Chem.* 277: 26501-26507 (2002); U.S. Pat. No. 7,323,336. The advantageous properties of the Fuelzyme®-LF alpha-amylase include: effective viscosity reduction at a lower dose, improved thermostability, and broad pH operating ranges. The use of this alpha-amylase, however, is currently limited to biofuel applications, e.g., ethanol production, because it results in ineffectual glucose syrup that is not suitable for downstream applications such as sweetener applications. Specifically, saccharification of starch liquefact from Fuelzyme®-LF alpha-amylase results in iodine-positive saccharide (IPS), which indicates incomplete starch hydrolysis. Thus, if a way could be found to fully exploit the advantages of the Fuelzyme®-LF alpha-amylase in starch processing, particularly in sweetener applications, by using an optimized blend of alpha-amylases, this would also represent a useful contribution to the art.

SUMMARY

Starch processing for high glucose syrup production by a low pH, thermostable alpha-amylase, e.g., Fuelzyme®-LF alpha-amylase, is unsatisfactory due to ineffectual starch hydrolysis. The present disclosure provides an enzyme blend comprising the low pH, thermostable alpha-amylase, e.g., Fuelzyme®-LF alpha-amylase, and a *Bacillus licheniformis* alpha-amylase. When used in starch processing, the enzyme blend eliminates iodine-positive saccharide (IPS; blue saccharide) resulted from using the low pH, thermostable alpha-amylase alone. Therefore, the enzyme blend produces saccharified starch suitable for downstream applications, such as sweetener production.

The enzyme blend for processing a starch as contemplated herein comprises a low pH, thermostable alpha-amylase, e.g., Fuelzyme®-LF alpha-amylase, and a *Bacillus licheniformis* alpha-amylase. The low pH, thermostable alpha-amylase has an amino acid sequence that is at least about 80%, about 85%, about 90%, about 95%, about 98%, or about 99% identical to SEQ ID NO: 2. The enzyme blend contains at least about 0.5, about 1.0, about 1.1, about 1.2, about 1.3, about 1.4, about 1.5, about 1.6, about 1.7, about 1.8, about 1.9, about 2.0, about 2.5, about 3.0, about 3.5, about 4.0, about 4.5, or about 5.0 Liquefon Units (LUs) of the *B. licheniformis* alpha-amylase for every 5.0 Modified Wohlgemuth Units (MWUs) of the low pH, thermostable alpha-amylase. At least one alpha-amylase of the enzyme blend may be purified. Optionally, the enzyme blend may further comprise a phytase.

In one aspect, disclosed is a method of processing a starch or grain, comprising contacting the enzyme blend to a starch and liquefying the starch to form a liquefact. In another aspect, disclosed is a method of processing a starch by contacting the low pH, thermostable alpha-amylase and the *B. licheniformis* alpha-amylase, simultaneously or sequentially, to a starch and liquefying the starch to form a liquefact. During liquefying the starch, the *B. licheniformis* alpha-amylase is used at an amount of about 0.5, about 1.0, about 1.1, about 1.2, about 1.3, about 1.4, about 1.5, about 1.6, about 1.7, about 1.8, about 1.9, about 2.0, about 2.5, about 3.0, about 3.5, about 4.0, about 4.5, or about 5.0 Liquefon Units (LUs) for every 5.0 Modified Wohlgemuth Units (MWUs) of the low pH, thermostable alpha-amylase per gram of dry solid starch (/g DS). The liquefaction results in a liquefact having a DE value of at least about 10, about 11, about 12, about 13, about 14, about 15, about 16, about 17, about 18, about 19, or about 20 within about 90 minutes, about 95 minutes, or about 100 minutes. The starch may be liquefied at about 80° C. to about 95° C., about 85° C. to about 95° C., or about 88° C. to about 92° C. The starch may be liquefied at about pH 5.0 to about pH 6.0, pH 5.2 to about ph 5.8, or optionally about pH 5.6.

The *B. licheniformis* alpha-amylase has an amino acid sequence that is at least about 70%, about 75%, about 80%, about 85%, about 90%, about 95%, about 98%, or about 99% identical to SEQ ID NO: 4. The *B. licheniformis* alpha-amylase may comprise an amino acid sequence of SEQ ID NO: 6. The *B. licheniformis* alpha-amylase may consist of an amino acid sequence of SEQ ID NO: 6. The *B. licheniformis* alpha-amylase may be a variant having one or more altered properties compared to the *B. licheniformis* alpha-amylase having a amino acid sequence of SEQ ID NO: 4. The altered properties may include substrate specificity, substrate binding, substrate cleavage pattern, thermal stability, pH activity profile, pH stability profile, stability towards oxidation, stability at lower levers of calcium ion ($Ca^{2+}$), specific activity, or any combination thereof. The low pH, thermostable alpha-amylase of the disclosed enzyme blend may comprise an amino acid sequence of SEQ ID NO: 2. Alternatively, the low pH, thermostable alpha-amylase of the disclosed enzyme blend may consist of an amino acid sequence of SEQ ID NO: 2.

Also contemplated is a method of processing a starch or grain further comprising saccharifying the liquefact to generate a saccharide syrup. The saccharide syrup may contain at least about 90%, about 91%, about 92%, about 93%, about 94%, or about 95% glucose at the end of saccharification. The saccharide syrup may contain less than about 1.5%, about 1.0%, or about 0.5% v/v sediment. Moreover, the saccharified starch may have a filtration rate at least about 67 g/15 minutes, about 75 g/15 minutes, about 80 g/15 minutes, about 85 g/15 minutes, or about 90 g/15 minutes.

Another contemplated aspect is a method of processing a starch or grain further comprising producing a high fructose syrup from the saccharide syrup. The high fructose syrup may be produced by contacting a glucose isomerase to the saccharide syrup. The glucose isomerase may be immobilized on a solid support.

BRIEF DESCRIPTION OF THE DRAWINGS

FIG. 1 depicts the results of iodine test performed with saccharified starch substrates from liquefact samples catalyzed by (1) 50 MWUs Fuelzyme®-LF/g ds starch at pH 4.5, (2) 50 MWUs Fuelzyme®-LF/g ds starch at pH 5.6, (3) 25 MWUs Fuelzyme®-LF/g ds starch at pH 5.6, (4) 10 LUs SPEZYME® FRED (Danisco US Inc., Genencor Division)/g ds starch at pH 5.8, and (5) 25 MWUs Fuelzyme®-LF/g ds starch supplemented with 5 LUs SPEZYME® FRED/g ds starch at pH 5.6.

DETAILED DESCRIPTION

An enzyme blend of a low pH, thermostable alpha-amylase and a *Bacillus licheniformis* alpha-amylase is provided. The enzyme blend contains about 0.5, about 1.0, about 1.1, about 1.2, about 1.3, about 1.4, about 1.5, about 1.6, about 1.7, about 1.8, about 1.9, about 2.0, about 2.5, about 3.0, about 3.5, about 4.0, about 4.5, or about 5.0 Liquefon Units (LUs) of the *B. licheniformis* alpha-amylase for every 5.0 Modified Wohlgemuth Units (MWUs) of the low pH, thermostable alpha-amylase. The enzyme blend is suitable for liquefying starch and further downstream applications of starch processing, e.g., sweetener applications. Also provided is a method of processing a starch by contacting the low pH, thermostable alpha-amylase and the *Bacillus licheniformis* alpha-amylase to the starch and liquefying the starch to form a liquefact. During liquefying the starch, the amount of the *B. licheniformis* alpha-amylase is about 0.5, about 1.0, about 1.1, about 1.2, about 1.3, about 1.4, about 1.5, about 1.6, about 1.7, about 1.8, about 1.9, about 2.0, about 2.5, about 3.0, about 3.5, about 4.0, about 4.5, or about 5.0 Liquefon Units (LUs) for every 5.0 Modified Wohlgemuth Units (MWUs) of the low pH, thermostable alpha-amylase.

1. Definitions & Abbreviations 1.1. Definitions

As used herein, "starch" refers to any material comprised of the complex polysaccharide carbohydrates of plants, comprised of amylose and amylopectin with the formula $(C_6H_{10}O_5)_x$, wherein X can be any number. In particular, the term refers to any plant-based material including but not limited to grains, grasses, tubers, and roots and more specifically wheat, barley, corn, rye, oats, sorgum, milo, rice, sorghum, brans, cassava, millet, potato, sweet potato, and tapioca.

"Alpha-amylase" (e.g., E.C. 3.2.1.1) generally refers to enzymes that catalyze the hydrolysis of alpha-1,4-glucosidic linkages. These enzymes have also been described as those effecting the exo- or endohydrolysis of 1,4-α-D-glucosidic linkages in polysaccharides containing 1,4-α-linked D-glucose units. For the purpose of the present disclosure, "alpha-amylases" refers to those enzymes having relatively high thermostability, i.e., with sustained activity at higher temperatures, e.g., above 80° C. Accordingly, alpha-amylases are capable of liquefying starch, which is performed at a temperature above 80° C.

"Alpha-amylase unit" (AAU) refers to alpha-amylase activity measured according to the method disclosed in U.S. Pat. No. 5,958,739, which is incorporated herein by reference. One unit of AAU refers to the amount of enzyme required to hydrolyze 10 mg of starch per minute under specified conditions. The assay for alpha-amylase activity uses p-nitrophenyl maltoheptoside (PNP-$G_7$) as the substrate with the non-reducing terminal sugar chemically blocked. PNP-$G_7$ can be cleaved by an endo-amylase, for example alpha-amylase. Following the cleavage, an alpha-glucosidase and a glucoamylase digest the substrate to liberate free PNP molecules, which display a yellow color and can be measured by visible spectophometry at 410 nm. The rate of PNP release is proportional to alpha-amylase activity. The AAU of a given sample is calculated against a standard control.

As used herein, "Liquefon unit" (LU) refers to the digestion time required to produce a color change with iodine solution, indicating a definite stage of dextrinization of starch substrate under standard assay conditions. In brief, the substrate can be soluble Lintner starch 5 g/L in phosphate buffer, pH 6.2 (42.16 g/liter potassium dihydrogen phosphate, 3.16 g/liter sodium hydroxide). The sample is added in 25 mM calcium chloride and activity is measured as the time taken to give a negative iodine test upon incubation at 30° C. Activity is recorded in liquefons per gram or mL (LU) calculated according to the formula:

$$LU/mL \text{ or } LU/g = \frac{570}{V \times t} \times D$$

Where LU=liquefon unit; V=volume of sample (5 mL); t=dextrinization time (minutes); D=dilution factor=dilution volume/mL or g of added enzyme.

One "Modified Wohlgemuth unit" (MWU) refers to the amount of enzyme, e.g., Fuelzyme®-LF, which is able to hydrolyze 1 mg of soluble starch to specific dextrins under standard reaction conditions in 30 minutes. See also Diversa Corp., URL at >>http://www.diversa.com/pdf/Fuelzyme-LF_Brochure.pdf.<<

As used herein, an enzyme "blend" refers to a mixture comprising at least two enzymes, for example, two alpha-amylases.

"Pullulanase" refers to an amylolytic endoenzyme, capable of catalyzing the hydrolysis of the α-1,6-glucosidic bonds. Pullulanases are able to degrade pullulan, which is regarded as a chain of maltotriose units linked by α-1,6-glucosidic bonds. Pullulanases are also called debranching enzymes (E.C. 3.2.1.41; pullulan 6-glucanohydrolase) capable of hydrolyzing α-1,6-glucosidic linkage in an amy-lopectin molecule. These enzymes are generally secreted by Bacillus species, e.g., Bacillus deramificans (U.S. Pat. No. 5,817,498), Bacillus acidopullulyticus (European Patent Application No. 82302001.1 (Publication No. 0063909)), and Bacillus naganoensis (U.S. Pat. No. 5,055,403). Commercially available enzymes having pullulanase activity include, for example, OPTIMAX® L-1000 (Danisco US Inc., Genencor Division) and Promozyme® (Novozymes A/S).

As used herein, "iodine-positive saccharide" (IPS), used interchangeably with "starch-positive saccharide" or "blue saccharide," refers to saccharification liquor containing amylose that is not hydrolyzed after liquefaction and saccharification. When saccharified starch is tested with iodine, the high DPn amylose binds iodine and produces a characteristic blue color. IPS is highly undesirable in starch processing application, particularly in sweetener applications. Specifically, IPS indicates poor liquefaction, i.e., incomplete starch hydrolysis. IPS results in actual production loss due to fining out. IPS also plugs or slows filtration system, and fouls the carbon columns used for purification. When IPS reaches sufficiently high levels, it may leak through the carbon columns and decrease production efficiency. Additionally, it may results in hazy final product upon storage, which is unacceptable for final product quality.

The term "recombinant" when used in reference to a cell, nucleic acid, protein or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell, or express native genes that are otherwise abnormally expressed, under expressed or not expressed at all.

The terms "protein" and "polypeptide" are used interchangeably herein.

The conventional one-letter or three-letter code for amino acid residues is used herein.

A "signal sequence" means a sequence of amino acids bound to the N-terminal portion of a protein, which facilitates the secretion of the mature form of the protein outside the cell. The definition of a signal sequence is a functional one. The mature form of the extracellular protein lacks the signal sequence that is cleaved off during the secretion process.

A "gene" refers to a DNA segment that is involved in producing a polypeptide and includes regions preceding and following the coding regions as well as intervening sequences (introns) between individual coding segments (exons).

The term "nucleic acid" encompasses DNA, RNA, single stranded or double stranded and chemical modifications thereof. The terms "nucleic acid" and "polynucleotide" may be used interchangeably herein.

A "vector" refers to a polynucleotide sequence designed to introduce nucleic acids into one or more cell types, wherein the elements of the vector are operably linked Vectors include cloning vectors, expression vectors, shuttle vectors, plasmids, phage particles, cassettes and the like.

An "expression vector" as used herein means a DNA construct comprising a DNA sequence that is operably linked to a suitable control sequence capable of effecting expression of the DNA in a suitable host. Such control sequences may include a promoter to effect transcription, an optional operator sequence to control transcription, a sequence encoding suitable ribosome binding sites on the mRNA, enhancers and sequences that control termination of transcription and translation.

A "promoter" is a regulatory sequence that is involved in binding RNA polymerase to initiate transcription of a gene. The promoter may be an inducible promoter or a constitutive promoter.

"Under transcriptional control" is a term well understood in the art that indicates that transcription of a polynucleotide sequence, usually a DNA sequence, depends on its being operably linked to an element that contributes to the initiation of, or promotes transcription.

"Under translational control" is a term well understood in the art that indicates a regulatory process that occurs after mRNA has been formed.

As used herein, when describing proteins and genes that encode them, the term for the gene is italicized, (e.g., the gene that encodes amyL (B. licheniformis AA) may be denoted as amyL). The term for the protein is generally not italicized and the first letter is generally capitalized (e.g., the protein encoded by the amyL gene may be denoted as AmyL or amyL).

The term "derived" encompasses the terms "originated from," "obtained" or "obtainable from," and "isolated from."

The term "operably linked" refers to juxtaposition wherein the elements are in an arrangement allowing them to be functionally related. For example, a promoter is operably linked to a coding sequence if it controls the transcription of the sequence.

The term "selective marker" refers to a gene capable of expression in a host that allows for ease of selection of those hosts containing an introduced nucleic acid or vector. Examples of selectable markers include but are not limited to antimicrobials (e.g., hygromycin, bleomycin, or chloramphenicol) and/or genes that confer a metabolic advantage, such as a nutritional advantage on the host cell.

A polynucleotide or a polypeptide having a certain percent (e.g., about 80%, about 85%, about 90%, about 95%, or about 99%) of sequence identity with another sequence means that, when aligned, that percentage of bases or amino acid residues are the same in comparing the two sequences. This alignment and the percent homology or identity can be determined using any suitable software program known in the art, for example those described in CURRENT PROTOCOLS IN MOLECULAR BIOLOGY, Ausubel et al., eds., 1987, Supplement 30, section 7.7.18. Representative programs include the Vector NTI Advance™ 9.0 (Invitrogen Corp. Carlsbad, Calif.), GCG Pileup, FASTA (Pearson et al. (1988) Proc. Nat'l Acad. Sci. USA 85:2444-2448), and BLAST (BLAST Manual, Altschul et al., Nat'l Cent. Biotechnol. Inf., Nat'l Lib. Med. (NCIB NLM NIH), Bethesda, Md., and Altschul et al., (1997) Nucleic Acids Res. 25:3389-3402) programs. Another typical alignment program is ALIGN Plus (Scientific and Educational Software, PA), generally using default parameters. Another sequence software program that finds use is the TFASTA Data Searching Program available in the Sequence Software Package Version 6.0 (Genetics Computer Group, University of Wisconsin, Madison, Wis.).

The term "parent" or "parent sequence" refers to a sequence that is native or naturally occurring in a host cell. Parent sequences include, but are not limited to, the sequences of Bacillus licheniformis alpha-amylase LAT (SEQ ID NO: 4), which is incorporated herein by reference.

"Variants" may have at least about 45%, at least about 50%, at least about 55%, at least about 60%, at least about 65%, at least about 70%, at least about 75%, at least about 80%, at least about 85%, at least about 88%, at least about 90%, at least about 91%, at least about 92%, at least about 93%, at least about 94%, at least about 95%, at least about 96%, at least about 97%, at least about 98%, at least about 99%, or at least about 99.5% sequence identity to a polypeptide sequence when optimally aligned for comparison.

The term "property" or grammatical equivalents thereof in the context of a polypeptide, as used herein, refers to any characteristic or attribute of a polypeptide that can be selected or detected. These properties include, but are not limited to oxidative stability, substrate specificity, catalytic activity, thermal stability, pH activity profile, resistance to proteolytic degradation, $K_M$, $k_{cAT}$, $k_{cAT}/K_m$ ratio, protein folding, ability to bind a substrate and ability to be secreted.

"Thermostable" or "thermostability" means the enzyme retains active after exposure to elevated temperatures. The thermostability of an alpha-amylase is evaluated by its half-life ($t_{1/2}$), where half of the enzyme activity is lost at a given temperature. The half-life is measured by determining the specific alpha-amylase activity of the enzyme remaining over time at a given temperature, particularly at a temperature used for a specific application, e.g., liquefaction.

"Host strain" or "host cell" means a suitable host for an expression vector or a DNA construct comprising a polynucleotide encoding a variant alpha-amylase enzyme according to the present disclosure. Specifically, host strains are typically bacterial cells. In a typical embodiment, "host cell" means both the cells and protoplasts created from the cells of a microbial strain and particularly a Bacillus sp.

The term "culturing" refers to growing a population of microbial cells under suitable conditions in a liquid or solid medium. In one embodiment, culturing refers to fermentative bioconversion of a starch substrate containing granular starch to an end product (typically in a vessel or reactor). Fermentation is the enzymatic and anaerobic breakdown of organic substances by microorganisms to produce simpler organic compounds. While fermentation occurs under anaerobic conditions it is not intended that the term be solely limited to strict anaerobic conditions, as fermentation also occurs in the presence of oxygen.

The term "enzymatic conversion" in general refers to the modification of a substrate by enzyme action. The term as used herein also refers to the modification of a starch substrate by the action of an enzyme.

As used herein, "Baumé degrees" refer to the specific gravity of a liquid. At 20° C., the relationship between specific gravity (s.g.) and Baumé degrees is:

for liquids heavier than water: s.g.=145÷(145−Baumé degrees); and for liquids lighter than water: s.g.=140÷(Baumé degrees+130).

For starch suspensions, e.g., slurries and starch hydrolysates, the Baumé-dry substance relationship is disclosed in Cleland J. et al., "Baumé-Dry Substance Tables for Starch Suspensions," Ind. Eng. Chem. anal. Ed., 15: 334-36 (1943). See also, "Critical Data Tables," Corn Refiners Association, Inc. (1991). Baumé degrees are useful in the corn wet milling industry for both process control and commercial sale of hydrolysis products.

As used herein, "saccharification" refers to enzymatic conversion of starch to glucose.

"Gelatinization" means solubilization of a starch molecule by cooking to form a viscous suspension.

"Liquefaction" refers to the stage in starch conversion in which gelatinized starch is hydrolyzed to give low molecular weight soluble dextrins.

The term "degree of polymerization (DP)" refers to the number (n) of anhydroglucopyranose units in a given saccharide. Examples of DP1 are the monosaccharides, such as glucose and fructose. Examples of DP2 are the disaccharides, such as maltose and sucrose. A DP>3 denotes polymers with a degree of polymerization of greater than 3.

The term "Dextrose Equivalent" (DE) value refers to the degree of hydrolysis of starch. It reflects the percentage of the total solids that have been converted to reducing sugars. A higher DE value underlies that more sugars and less dextrins are present. Along various stages of starch processing, glucose syrups having an above 55 DE value are termed high conversion; between 35-55, regular conversion; below 20, the products of hydrolysis are maltins or maltodextrins.

The terms "end product" or "desired end product" refer to any carbon-source derived molecule product that is enzymatically converted from the starch substrate.

As used herein the term "dry solids content (ds)" refers to the total solids of a slurry in % on a dry weight basis.

The term "slurry" refers to an aqueous mixture containing insoluble solids.

The term "residual starch" refers to the remaining starch (soluble or insoluble) left in a composition after fermentation of a starch-containing substrate.

As used herein, "a recycling step" refers to the recycling of mash components, which may include residual starch, enzymes and/or microorganisms to ferment substrates comprising starch.

The term "mash" refers to a mixture of a fermentable carbon source (carbohydrate) in water used to produce a fermented product, such as an alcohol. In some embodiments, the term "beer" and "mash" are used interchangeability.

The term "stillage" means a mixture of non-fermented solids and water, which is the residue after removal of alcohol from a fermented mash.

The terms "distillers dried grain (DDG)" and "distillers dried grain with solubles (DDGS)" refer to a useful by-product of grain fermentation.

As used herein, "ethanologenic microorganism" refers to a microorganism with the ability to convert a sugar or oligosaccharide to ethanol. The ethanologenic microorganisms are ethanologenic by virtue of their ability to express one or more enzymes that individually or together convert sugar to ethanol.

As used herein, "ethanol producer" or "ethanol producing microorganism" refers to any organism or cell that is capable of producing ethanol from a hexose or pentose. Generally, ethanol-producing cells contain an alcohol dehydrogenase and a pyruvate decarboxylase. Examples of ethanol producing microorganisms include fungal microorganisms such as yeast. The typical yeast used in ethanol production includes strains of *Saccharomyces*, e.g., *S. cerevisiae*.

The term "heterologous" with reference to a polynucleotide or protein refers to a polynucleotide or protein that does not naturally occur in a host cell. In some embodiments, the protein is a commercially important industrial protein. It is intended that the term encompass proteins that are encoded by naturally occurring genes, mutated genes, and/or synthetic genes.

The term "endogenous" with reference to a polynucleotide or protein refers to a polynucleotide or protein that occurs naturally in the host cell.

The terms "recovered," "isolated," and "separated" as used herein refer to a compound, protein, cell, nucleic acid or amino acid that is removed from at least one component with which it is naturally associated.

As used herein, "transformed," "stably transformed" and "transgenic" used in reference to a cell means the cell has a non-native (e.g., heterologous) nucleic acid sequence integrated into its genome or as an episomal plasmid that is maintained through multiple generations.

As used herein, "expression" refers to the process by which a polypeptide is produced based on the nucleic acid sequence of a gene. The process includes both transcription and translation.

The term "introduced" in the context of inserting a nucleic acid sequence into a cell, means "transfection," or "transformation" or "transduction" and includes reference to the incorporation of a nucleic acid sequence into a eukaryotic or prokaryotic cell wherein the nucleic acid sequence may be incorporated into the genome of the cell (e.g., chromosome, plasmid, plastid, or mitochondrial DNA), converted into an autonomous replicon, or transiently expressed (e.g., transfected mRNA).

As used herein, "specific activity" means an enzyme unit defined as the number of moles of substrate converted to product by an enzyme preparation per unit time under specific conditions. Specific activity is expressed as units (U)/mg of protein.

The term "yield" refers to the amount of end products or desired end products produced using the methods of the present disclosure. In some embodiments, the yield is greater than that produced using methods known in the art. In some embodiments, the term refers to the volume of the end product and in other embodiment, the term refers to the concentration of the end product.

As used herein, "contacting" or "admixing" refers to the placing of the respective enzyme(s) in sufficiently close proximity to the respective substrate to enable the enzyme(s) to convert the substrate to the end product. Those skilled in the art will recognize that mixing solutions of the enzyme with the respective substrates can effect contacting or admixing.

"ATCC" refers to American Type Culture Collection located at Manassas, Va. 20108 (ATCC). "NRRL" refers to the Agricultural Research Service Culture Collection, National Center for Agricultural Utilization Research (and previously known as USDA Northern Regional Research Laboratory), Peoria, Ill.

"A," "an," and "the" include plural references unless the context clearly dictates otherwise.

As used herein, "comprising" and its cognates are used in their inclusive sense; that is, equivalent to the term "including" and its corresponding cognates.

1.2. Abbreviations

The following abbreviations apply unless indicated otherwise:
AA alpha-amylase
AAU alpha-amylase unit
AOS α-olefinsulfonate
AS alcohol sulfate
BAA bacterial alpha-amylase
cDNA complementary DNA
CMC carboxymethylcellulose
DDG distillers dried grains
DDGS distillers dried grain with solubles
DE Dextrose Equivalent
DNA deoxyribonucleic acid
DNS 3,5-dinitrosalicylic acid
DP3 degree of polymerization with three subunits
DPn degree of polymerization with n subunits
DS, ds dry solid
DSC differential scanning calorimetry
DTMPA diethyltriaminepentaacetic acid
EC enzyme commission for enzyme classification
EDTA ethylenediaminetetraacetic acid
EDTMPA ethylenediaminetetramethylene phosphonic acid
EO ethylene oxide FRED SPEZYME® FRED (SEQ ID NO: 6) (Danisco US Inc., Genencor Division)
F&HC fabric and household care
g gram
gal gallon
GAU glucoamylase activity unit
HFCS high fructose corn syrup
HFSS high fructose starch based syrup
IPS iodine-positive saccharide (starch-positive saccharide)
IPTG isopropyl β-D-thiogalactoside
LAS linear alkylbenezenesulfonate
LAT *Bacillus licheniformis* alpha-amylase (SEQ ID NO: 4)
LU Liquefon units
MES 2-(N-morpholino)ethanesulfonic acid
MW molecular weight
MWU modified Wohlgemuth units
nm nanometer
NOBS nonanoyloxybenzenesulfonate
NTA nitrilotriacetic acid
PCR polymerase chain reaction
PEG polyethyleneglycol
pI isoelectric point
PNP-$G_7$ p-nitrophenyl maltoheptoside
ppm parts per million
PVA poly(vinyl alcohol)
PVP poly(vinylpyrrolidone)
RAU Reference Amylase Units
RMS root mean square
RNA ribonucleic acid
rpm revolutions per minute
SAS secondary alkane sulfonates
s.g. specific gravity
1×SSC 0.15 M NaCl, 0.015 M sodium citrate, pH 7.0
SSF simultaneous saccharification and fermentation
TAED tetraacetylethylenediamine
TNBS trinitrobenzenesulfonic acid
w/v weight/volume
w/w weight/weight
wt wild-type
μL microliter 2. Starch Processing 2.1. Starch Substrates and Raw Materials Those of skill in the art are well aware of available methods that may be used to prepare starch substrates for use in the processes disclosed herein. For example, a useful starch substrate may be obtained from tubers, roots, stems, legumes, cereals or whole grain. More specifically, the granular starch comes from plants that produce high amounts of starch. For example, granular starch may be obtained from corn, cobs, wheat, barley, rye, milo, sago, cassava, tapioca, sorghum, rice, peas, bean, banana, or potatoes. Corn contains about 60-68% starch; barley contains about 55-65% starch; millet contains about 75-80% starch; wheat contains about 60-65% starch; and polished rice contains about 70-72% starch. Specifically contemplated starch substrates are cornstarch, wheat starch, and barley starch. The starch from a grain may be ground or whole and includes corn solids, such as kernels, bran and/or cobs. The starch may be highly refined raw starch or feedstock from starch refinery processes. Various starches also are commercially available. For example, cornstarch is available from Cerestar, Sigma, and Katayama Chemical Industry Co. (Japan); wheat starch is available from Sigma; sweet potato starch is available from Wako Pure Chemical Industry Co. (Japan); and potato starch is available from Nakaari Chemical Pharmaceutical Co. (Japan).

2.2. Milling

The starch substrate can be a crude starch from milled whole grain, which contains non-starch fractions, e.g., germ residues and fibers. Milling may comprise either wet milling or dry milling. In wet milling, whole grain is soaked in water or dilute acid to separate the grain into its component parts, e.g., starch, protein, germ, oil, kernel fibers. Wet milling efficiently separates the germ and meal (i.e., starch granules and protein) and is especially suitable for production of syrups. In dry milling, whole kernels are ground into a fine powder and processed without fractionating the grain into its component parts. Dry milled grain thus will comprise significant amounts of non-starch carbohydrate compounds, in addition to starch. Most ethanol comes from dry milling. Alternatively, the starch to be processed may be a highly refined starch quality, for example, at least about 90%, at least about 95%, at least about 97%, or at least about 99.5% pure.

2.3. Gelatinization and Liquefaction

As used herein, the term "liquefaction" or "liquefy" means a process by which starch is converted to less viscous and shorter chain dextrins. This process involves gelatinization of starch simultaneously with or followed by the addition of alpha-amylases. Additional liquefaction-inducing enzymes, e.g., a phytase, optionally may be added.

In some embodiments, the starch substrate prepared as described above is slurried with water. The starch slurry may contain starch as a weight percent of dry solids of about 10-55%, about 20-45%, about 30-45%, about 30-40%, or about 30-35%. To optimize alpha-amylase stability and activity, the pH of the slurry may be adjusted to the optimal pH for the alpha-amylases. Alpha-amylases remaining in the slurry following liquefaction may be deactivated by lowering pH in a subsequent reaction step or by removing calcium from the slurry.

The slurry of starch plus the alpha-amylases may be pumped continuously through a jet cooker, which is steam heated from about 85° C. to up to about 105° C. Gelatinization occurs very rapidly under these conditions, and the enzymatic activity, combined with the significant shear forces, begins the hydrolysis of the starch substrate. The residence time in the jet cooker is very brief. The partly gelatinized starch may be passed into a series of holding tubes maintained at about 85-105° C. and held for about 5 min to complete the gelatinization process. These tanks may contain baffles to discourage back mixing. As used herein, the term "secondary liquefaction" refers the liquefaction step subsequent to primary liquefaction, when the slurry is allowed to cool to room temperature. This cooling step can be about 30 minutes to about 180 minutes, e.g., about 90 minutes to 120 minutes. Milled and liquefied grain is also known as mash.

2.4. Saccharification

Following liquefaction, the mash is further hydrolyzed through saccharification to produce high glucose syrup that can be readily used in the downstream applications. The pH of the liquefied starch is generally adjusted to pH 4.2 to pH 4.5 using diluted sulfuric acid, and the liquefied starched is then incubated at 60° C. for 36 to 96 hours. During saccharification, the hydrolysis is generally accomplished enzymatically by the presence of saccharification enzymes, i.e., a blend of glucoamylase and pullulanase. Representative blends of saccharification enzymes are OPTIMAX® 4060 VHP (Danisco US Inc., Genencor Division) and Dextrozyme® DX (Novozymes A/S). Typically, an alpha-glucosidase and/or an acid alpha-amylase may also be supplemented in addition of the saccharification enzyme blend.

A full saccharification step may typically range 24 to 96 hours. In some embodiments for ethanol production, the saccharification step and fermentation step are combined and the process is referred to as simultaneous saccharification and fermentation (SSF) or simultaneous saccharification, yeast propagation and fermentation. In some embodiments, a pre-saccharification step of about 1-4 hours may be included between the liquefaction step and the following saccharification/fermentation step.

2.5. Sweetener Production

When the desired final product from starch processing is high fructose starch-based syrup (HFSS), e.g., high fructose corn syrup (HFCS), the dextrose syrup from the saccharification process may be converted into fructose. The conversion is typically catalyzed by a glucose isomerase, e.g., GENSWEET® (Danisco US Inc., Genencor Division) and Sweetzyme® (Novozymes, A/S). In brief, after the saccharification process, the pH is increased to a value in the range of about 6-8, typically about 7.5, and the calcium is removed by ion exchange. The dextrose syrup is then converted into high fructose syrup using, e.g., a glucose isomerases immobilized on a solid support, such as GENSWEET® IGI-HF (Danisco US Inc., Genencor Division).

3. Alpha-Amylases 3.1. Structure and Function

Alpha-amylases constitute a group of enzymes present in microorganisms and tissues from animals and plants. They are capable of hydrolyzing alpha-1,4-glucosidic bonds of glycogen, starch, related polysaccharides, and some oligosaccharides. Although all alpha-amylases possess the same catalytic function, their amino acid sequences vary greatly. The sequence identity between different amylases can be virtually non-existent, e.g., falling below 25%. Despite considerable amino acid sequence variation, alpha-amylases share a common overall topological scheme that has been identified after the three-dimensional structures of alpha-amylases from different species have been determined. The common three-dimensional structure reveals three domains: (1) a "TIM" barrel known as domain A, (2) a long loop region known as domain B that is inserted within domain A, and (3) a region close to the C-terminus known as domain C that contains a characteristic beta-structure with a Greek-key motif. See van der Maarel et al., *J. Biotechnol.* 94: 137-55 (2002).

The TIM barrel of domain A consists of eight alpha-helices and eight parallel beta-strands, i.e., $(\beta/\alpha)_8$, that alternate along the peptide backbone. This structure, named after a conserved glycolytic enzyme triosephosphate isomerase, has been known to be common among conserved protein folds. Domain B is a loop region inserted between $\beta_{A3}$ and $\alpha_{A3}$ (the third β-strand and α-helix in domain A). Both domain A and domain B are directly involved in the catalytic function of an alpha-amylase, because the three-dimensional structure indicates that domain A flanks the active site and domain overlays the active site from on side. Furthermore, domain A is considered the catalytic domain, as amino acid residues of the active site are located in loops that link beta-strands to the adjacent alpha-helices. Domain B is believed to determine the specificity of the enzyme by affecting substrate binding. MacGregor et al., *Biochim. Biophys. Acta.* 1546:1-20 (2001).

3.2. Fuelzyme®-LF Alpha-Amylases

One of the component of the presently described enzyme blend is the Fuelzyme®-LF alpha-amylase (SEQ ID NO: 2), or an alpha-amylase that has about 80%, about 85%, about 90%, about 95%, about 98%, about 99%, or about 99.5% amino acid sequence identity to the Fuelzyme®-LF alpha-amylase.

Fuelzyme®-LF alpha-amylase (SEQ ID NO: 2) is an engineered enzyme resulted from a three-parent DNA shuffling. See Richardson et al., *J. Biol. Chem.* 277: 26501-26507 (2002); U.S. Pat. No. 7,323,336. The DNA encoding the parent enzymes was collected from microorganisms inhabiting a deep-sea hydrothermal vent. The 16 S rRNA analysis suggested that the microorganisms belong to or have a very close relationship with *Thermococcus* sp. Fuelzyme®-LF alpha-amylase has been characterized for (1) its superior liquefaction and viscosity reduction capability, and (2) its broad temperature and pH operating ranges. See, Sheridan C., "It Came From Beneath The Sea," *Nat. Biotechnol.*, 23: 1199-201 (2005). The DNA sequence for Fuelzyme®-LF alpha-amylase and its genetic manipulation have been disclosed in U.S. Pat. Nos. 7,202,057; 7,273,740; 7,323,336; and 7,407, 677; all of which are incorporated herein by reference. Similarly, the production and purification of Fuelzyme®-LF alpha-amylase or related enzymes have been described in detail in the above issued U.S. patents.

However, Fuelzyme®-LF alpha-amylase is presently limited in the production of biofuels, e.g., ethanol production, because it results in ineffectual glucose syrup. Specifically, saccharification of starch liquefact resulted from Fuelzyme®-LF alpha-amylase yielded iodine-positive saccharide (IPS) or blue saccharide. See Examples infra. Such an observation indicates that the saccharified starch is not suitable for sweetener applications, e.g., production of high glucose or fructose syrup.

3.3. *B. licheniformis* Alpha-Amylase and Variants Thereof

Another component of the presently described enzyme blend may be a Termamyl-like alpha-amylase from *B. licheniformis*. In one aspect, the *B. licheniformis* alpha-amylases may be wild-type parent enzymes, e.g., the alpha-amylase having an amino acid sequence of SEQ ID NO: 4. In another aspect, the alpha-amylase may be a variant of the parent enzyme. The variant alpha-amylase may contain one or more modifications of the amino acid sequence of a wild-type *b. licheniformis* alpha-amylase. A wild-type *B. licheniformis* alpha-amylase may be isolated from any naturally occurring strain of *B. licheniformis*. For the purpose of this disclosure, an amino acid substitution may be designated M15T, for instance. "M15T" means that a methionine (M) residue at position 15 is replaced with a threonine (T) residue, where the amino acids are designated by single letter abbreviations commonly known in the art.

A particularly useful alpha-amylase from *B. licheniformis* is SPEZYME® FRED (SEQ ID NO: 6), commercially available from Danisco US Inc., Genencor Division. This alpha-amylase may be referred to herein as "FRED" (SEQ ID NO: 6).

Protein engineering of a wild-type *B. licheniformis* alpha-amylase generates variant alpha-amylases that can have improved properties. In one aspect, one or more amino acid residues of the variant enzyme are modified randomly, and the effect of the modifications is determined by subsequent analysis of the performance characteristics of the variant, following host cell expression of the variant. In another aspect, modifications to the amino acid sequence of the variant are made systematically, using a "model" alpha-amylase having a structure very similar to the wild-type *B. licheniformis* alpha-amylase as a guide, so that the effect of the modifications can be predicted.

If a model alpha-amylase is used to guide the design of amino acid changes of the variant alpha-amylase, it is not necessary to know precisely which residues of the model alpha-amylase contribute to the performance of the enzyme. Instead, one or more amino acids, even an entire set of amino acids, are modified in the variant alpha-amylase to the corresponding amino acid(s) of the model alpha-amylase. A "corresponding" amino acid in this case is not determined by a conventional alignment of the primary amino acid sequence, but by a three-dimensional structural alignment of the polypeptide backbone of the two enzymes Amino acids to be modified in the variant thus can be chosen as charged residues on the enzyme surface, active site residues, or residues that contribute to particular secondary structural elements unique to the model enzyme, for example. The residues to be modified also can be selected on the basis that the modification would not disrupt conserved three-dimensional structures between the two enzymes, particularly conserved secondary structural elements, e.g., α-helices, β-sheets, turns.

For example, it is known that changing the distribution of charged amino acids on the surface of an enzyme generally can alter its enzymatic properties. See, e.g., Russell et al., "Rational modification of enzyme catalysis by engineering surface charge," Nature 328: 496-500 (1987). One or more residues on the surface of the B. licheniformis alpha-amylase likewise can be modified to alter the enzymatic properties of the variant alpha-amylase, where the choice of modifications can be guided by the distribution of surface charges on the model alpha-amylase. For this purpose, a "surface charge" is contributed by a charged side chain of an amino acid that is at least partially exposed to solvent.

A residue of the variant alpha-amylase can be classified as belonging to one of three structural domains, herein called domains A, B and C. For the purpose of this disclosure, domain A extends from residues 2-105 and from residues 208-396; domain B extends from residues 106-207; and domain C extends from residue 397 to the C terminus of the protein. An amino acid also can be classified as an active site residue. Active site residues are located at least at positions 49, 52, 163, 167, 170, 172, 187, 188, 190, 238, 262, 264, 293, 297, and 332-334. Residue "positions" are numbered as depicted in the B. licheniformis alpha-amylase sequence (SEQ ID NO: 4).

In the variant alpha-amylase, one or more amino acid can be modified to the corresponding amino acid in the model alpha-amylase. The modifications may be clustered by domain, and/or they may be clustered by amino acids that are charged and present on the surface of the enzyme. Alternatively or in addition, modifications may be made to one or more active site residues. In this manner, it is possible to make multiple amino acid modifications, where the modifications have a predictable effect on the performance characteristics of the variant alpha-amylase. For example, the variant may have every surface charged residue in one or more domain changed to the corresponding residue of the model alpha-amylase. In another embodiment, the variant may have residues inserted or deleted, e.g., a loop may be inserted or deleted, such that the polypeptide backbone of the variant more closely resembles the structure of the model alpha-amylase. Accordingly, the variant may comprise 1, 2, 3, 4, 5, 10, 15, 20, 30, 40, 50, 60 or 70 amino acid substitutions, deletions or insertions, or any integer value in between, provided the variant retains alpha-amylase activity. The surface charge of the variant also may be altered by any number. For example, the number of positively charged amino acid residues on the enzyme surface may be reduced by 1, 2, 3, 4, 5, 6, 7 or 8. Such amino acid substitutions are expected to change the isoelectric point (pI) of the variant, among other things. Other characteristics of the variant may differ from the wild-type enzyme, as described below.

In another aspect, the variant alpha-amylase may have about a 50%, 55%, 60%, 65%, 70%, 75%, 80%, 85%, 90%, 95%, or 99% sequence identity to a Termamyl-like alpha-amylase from B. licheniformis. In another aspect, the variant alpha-amylase may have about a 50%, 55%, 60%, 65%, 70%, 75%, 80%, 85%, 90%, 95%, or 99% sequence identity to B. licheniformis alpha-amylase LAT (SEQ ID NO: 4). Contemplated variants are described in WO 95/35382, WO 96/23874, WO 97/41213, and WO 99/19467, all of which are incorporated herein by reference.

In yet another aspect, the blend may contain at least about 0.5, about 1.0, about 1.1, about 1.2, about 1.3, about 1.4, about 1.5, about 1.6, about 1.7, about 1.8, about 1.9, about 2.0, about 2.5, about 3.0, about 3.5, about 4.0, about 4.5, or about 5.0 Liquefon Units (LUs) of the B. licheniformis alpha-amylase for every 5.0 Modified Wohlgemuth Units (MWUs) of the low pH, thermostable alpha-amylase.

In another aspect, the variant alpha-amylase may have about a 50%, 55%, 60%, 65%, 70%, 75%, 80%, 85%, 90%, 95%, or 99% sequence identity to a Termamyl-like alpha-amylase.

In some embodiments, a variant B. licheniformis alpha-amylase may display one or more altered properties compared to those of the parent enzyme, e.g., the alpha-amylase having the amino acid sequence of SEQ ID NO: 4. The altered properties may advantageously enable the variant alpha-amylase to perform effectively in liquefaction. Similarly, the altered properties may result in improved performance of the variant compared to its parent. These properties may include substrate specificity, substrate binding, substrate cleavage pattern, thermal stability, pH/activity profile, pH/stability profile, stability towards oxidation, stability at lower levels of calcium ion ($Ca^{2+}$), and/or specific activity. Representative alpha-amylase variants, which can be useful in the present disclosure, include, but are not limited to those described in US 2008/0220476, published Sep. 11, 2008; US 2008/0160573, published Jul. 3, 2008; US 2008/0153733, published Jun. 26, 2008; US 2008/0083406, published Apr. 10, 2008; U.S. Ser. No. 12/263,804, filed Nov. 3, 2008; and U.S. Ser. No. 12/263,886, filed Nov. 3, 2008; all of which are incorporated herein by reference.

Alpha-amylase activity may be determined according to the method disclosed in U.S. Pat. No. 5,958,739, with minor modifications. In brief, the assay uses p-nitrophenyl maltoheptoside (PNP-$G_7$) as the substrate with the non-reducing terminal sugar chemically blocked. PNP-$G_7$ can be cleaved by an endo-amylase, for example alpha-amylase. Following the cleavage, an alpha-glucosidase and a glucoamylase digest the substrate to liberate free PNP molecules, which display a yellow color and can be measured by visible spectophometry at 410 nm. The rate of PNP release is proportional to alpha-amylase activity. The alpha-amylase activity of a sample is calculated against a standard control.

Enzyme variants can be characterized by nucleic acid and polypeptide sequences, by their 3D structures as described above, and/or by their specific activity. Additional features of the alpha-amylase variant include substrate specificity, half-life, stability at lower levels of calcium ion ($Ca^{2+}$), pH range, oxidation stability, and thermostability. In one aspect, the alpha-amylase variants may have higher specific activities, which can be assessed using standard assays known to the artisan skilled in this field. In another aspect, variants demonstrate other improved performance characteristics, such as improved stability at high temperatures (i.e., 70-120° C.), and/or pH extremes (i.e., about pH 4.0 to about 6.0 or about pH 8.0 to about 11.0), and/or calcium concentrations below about 60 ppm.

Altered substrate specificity may include altered substrate binding and/or altered substrate cleavage pattern. The altered substrate binding may refer to increased or decreased binding ability to a given substrate. Altered substrate cleavage pattern may refer to increased or decreased cleavage efficiency as compared to the parent enzyme.

Altered $Ca^{2+}$ stability means the stability of the enzyme under $Ca^{2+}$ depletion has been altered, i.e., increased or decreased. Mutations of importance include those that alter $Ca^{2+}$ stability and requirements, in particular those with decreased $Ca^{2+}$ dependence on at high pH, i.e., pH 8.0 to 10.5.

Altered pH profile means that the performance of the enzyme under different pH values has been altered. The altered pH profile may include altered pH activity profile, which refers to increased or decreased specific activity under a given range of pH. Additionally, altered pH profile may also include altered pH stability profile, which refers to increased or decreased stability under a given range of pH.

In a further aspect, important mutations exhibit altered specific activity, especially at temperatures from about 10° C. to about 60° C., particularly about 20° C. to about 50° C., and more particularly about 30° C. to about 40° C., for use in cleaning compositions.

Alpha-amylase variants also may have altered oxidation stability, in particular higher oxidation stability, in comparison to the parent alpha-amylase. For example, increased oxidation stability is advantageous in detergent compositions, and decreased oxidation stability may be advantageous in composition for starch liquefaction.

The variant alpha-amylase may be more thermostable than the wild-type alpha-amylase. Such alpha-amylase variants are advantageous for use in baking or other processes that require elevated temperatures. For example, a thermostable alpha-amylase variant can degrade starch at temperatures of about 55° C. to about 80° C. or more. A thermostable alpha-amylase variant may retain its activity after exposure to temperatures of up to about 95° C.

The alpha-amylase variant polypeptides described herein can also have mutations that extend half-life relative to the parent enzyme by at least about 10%, about 20%, about 30%, about 40%, about 50%, about 60%, about 70%, about 80%, about 90%, about 100%, about 200% or more, particularly at elevated temperatures of at least about 55° C. to about 95° C. or more, particularly at about 80° C. In one embodiment, the alpha-amylase variant can be heated for about 1-10 minutes at about 80° C. or higher.

The alpha-amylase variants may have exo-specificity, measured by exo-specificity indices described herein, for example. Alpha-amylase variants include those having higher or increased exo-specificity compared to the parent enzymes or polypeptides from which they were derived, typically when measured under identical conditions. Thus, for example, the alpha-amylase variant polypeptides may have an exo-specificity index of about 10%, about 20%, about 30%, about 40%, about 50%, about 60%, about 70%, about 80%, about 90%, about 100%, about 150%, about 200%, about 500%, about 1000%, about 5000%, about 10,000% or higher compared to their parent polypeptides.

In one aspect, the alpha-amylase variant polypeptide encoded by the nucleic acid has the same pH stability as the parental sequence. In another aspect, the variant comprises a mutation that confers a greater pH stability range or shifts the pH range to a desired area for the end commercial purpose of the enzyme. For example, in one embodiment, the variant can degrade starch at about pH 5.0 to about pH 10.5. The alpha-amylase variant polypeptide may have a longer half-life or higher activity (depending on the assay) compared to the parent polypeptide under identical conditions, or the alpha-amylase variant may have the same activity as the parent polypeptide. The alpha-amylase variant polypeptide also may have about 10%, 20%, 30%, 40%, 50%, 60%, 70%, 80%, 90%, 100%, 200% or longer half-life compared to their parent polypeptide under identical pH conditions. Alternatively, or in addition, the enzyme variant may have higher specific activity compared to the parent polypeptide under identical pH conditions.

In another aspect, a nucleic acid complementary to a nucleic acid encoding any of the alpha-amylase variants set forth herein is provided. Additionally, a nucleic acid capable of hybridizing to the complement is provided. In another embodiment, the sequence for use in the methods and compositions described here is a synthetic sequence. It includes, but is not limited to, sequences made with optimal codon usage for expression in host organisms, such as the methylotrophic yeasts *Pichia* and *Hansenula*.

4. Production and Purification of *B. licheniformis* Alpha-Amylases

A DNA sequence encoding the enzyme variant produced by methods described herein, or by any alternative methods known in the art, can be expressed, in enzyme form, using an expression vector which typically includes control sequences encoding a suitable promoter, operator, ribosome binding site, translation initiation signal, and, typically, a repressor gene or various activator genes.

4.1. Vectors

The recombinant expression vector carrying the DNA sequence encoding an alpha-amylase variant may be any vector that may conveniently be subjected to recombinant DNA procedures, and the choice of vector will often depend on the host cell into which it is to be introduced. Thus, the vector may be an autonomously replicating vector, i.e., a vector that exists as an extrachromosomal entity, the replication of which is independent of chromosomal replication, e.g., a plasmid, a bacteriophage or an extrachromosomal element, mini-chromosome or an artificial chromosome. Alternatively, the vector may be one which, when introduced into a host cell, is integrated into the host cell genome and replicated together with the chromosome(s) into which it has been integrated. The integrated gene may also be amplified to create multiple copies of the gene in the chromosome by use of an amplifiable construct driven by antibiotic selection or other selective pressure, such as an essential regulatory gene or by complementation of an essential metabolic pathway gene.

An expression vector typically includes the components of a cloning vector, e.g., an element that permits autonomous replication of the vector in the selected host organism and one or more phenotypically detectable markers for selection purposes. The expression vector normally comprises control nucleotide sequences encoding a promoter, operator, ribosome binding site, translation initiation signal and typically, a repressor gene or one or more activator genes. In one aspect, all the signal sequences used target the material to the cell culture media for easier enzyme collection and purification. The procedures used to ligate the DNA construct encoding an alpha-amylase variant, the promoter, terminator and other elements, respectively, and to insert them into suitable vectors containing the information necessary for replication, are well known to persons skilled in the art (see e.g., Sambrook et al., MOLECULAR CLONING: A LABORATORY MANUAL, $2^{nd}$ ed., Cold Spring Harbor, 1989 and $3^{rd}$ ed., 2001).

In the vector, the DNA sequence should be operably connected to a suitable promoter sequence. The promoter may be any DNA sequence that shows transcriptional activity in the host cell of choice and may be derived from genes encoding proteins either homologous or heterologous to the host cell. Examples of suitable promoters for directing the transcription of the DNA sequence encoding an alpha-amylase variant, especially in a bacterial host, are the promoter of the lac operon of *E. coli*, the *Streptomyces coelicolor* agarase gene dagA or celA promoters, the promoters of the *Bacillus licheniformis* alpha-amylase gene (amyL), the promoters of the *Bacillus stearothermophilus* maltogenic amylase gene (amyM), the promoters of the *Bacillus amyloliquefaciens* alpha-amylase (amyQ), the promoters of the *Bacillus subtilis* xylA and xylB genes, etc. For transcription in a fungal host, examples of useful promoters are those derived from the gene encoding *Aspergillus oryzae* TAKA amylase, *Rhizomucor miehei* aspartic proteinase, *Aspergillus niger* neutral alpha-amylase, *A. niger* acid stable alpha-amylase, *A. niger* glucoamylase, *Rhizomucor miehei* lipase, *A. oryzae* alkaline protease, *A. oryzae* triose phosphate isomerase, or *A. nidulans* acetamidase. When the gene encoding the alpha-amylase variant polypeptide is expressed in a bacterial species such as *E. coli*, a suitable promoter can be selected, for example, from a bacteriophage promoter including a T7 promoter and a phage lambda promoter. Examples of suitable promoters for the expression in a yeast species include but are not limited to the Gal 1 and Gal 10 promoters of *Saccharomyces cerevisiae* and the *Pichia pastoris* AOX1 or AOX2 promoters. For expression in *Trichoderma reesei*, the CBHII promoter also may be used.

The expression vector may also comprise a suitable transcription terminator and, in eukaryotes, polyadenylation sequences operably connected to the DNA sequence encoding the alpha-amylase variant. Termination and polyadenylation sequences may suitably be derived from the same sources as the promoter. The vector may further comprise a DNA sequence enabling the vector to replicate in the host cell in question. Examples of such sequences are the origins of replication of plasmids pUC19, pACYC177, pUB110, pE194, pAMB 1, pICatH, and pIJ702.

The vector may also comprise a selectable marker, e.g., a gene the product of which complements a defect in the host cell, such as the dal genes from *B. subtilis* or *B. licheniformis*, or a gene which confers antibiotic resistance, e.g., ampicillin, kanamycin, chloramphenicol or tetracyclin resistance. Furthermore, the vector may comprise *Aspergillus* selection markers such as amdS, argB, niaD and xxsC, a marker conferring hygromycin resistance, or the selection may be accomplished by co-transformation as known in the art. See, e.g., WO 91/17243.

4.2. Variant Expression and Host Organisms

While intracellular expression or solid-state fermentation may be advantageous in some respects, e.g., when using certain bacteria or fungi as host cells, it is generally advantageous if the expression of the variant is extracellular and into the culture medium. In general, the *Bacillus* alpha-amylases mentioned herein comprise a signal sequence that permits secretion of the expressed protease into the culture medium. If desirable, this signal sequence may be replaced by a different signal sequence, which is conveniently accomplished by substitution of the DNA sequences encoding the respective signal sequence. The signal sequences are typically characterized as having three domains, an N-terminal domain, an H-domain, and a C-terminal domain and range from 18 to 35 residues in length.

The mature protein can be in the form initially of a fusion protein to a pre-protein derived from another *Bacillus* sp. or from the same species as the parental sequence. To secrete proteins in *B. licheniformis*, the signal peptide of *B. licheniformis* alpha-amylase is frequently used; however, signal proteins from other *Bacillus* sp. alpha-amylases can also be substituted.

An isolated cell, comprising either a DNA construct or an expression vector, is advantageously used as a host cell in the recombinant production of an alpha-amylase variant. The cell may be transformed with the DNA construct encoding the variant, conveniently by integrating the DNA construct (in one or more copies) in the host chromosome. This integration is generally considered to be an advantage as the DNA sequence is more likely to be stably maintained in the cell. Integration of the DNA constructs into the host chromosome may be performed according to conventional methods, e.g., by homologous or heterologous recombination. Alternatively, the cell may be transformed with an expression vector as described above in connection with the different types of host cells.

Examples of suitable bacterial host organisms are Gram positive bacterial species such as Bacillaceae, including *B. subtilis, B. licheniformis, B. lentus, B. brevis, B. stearothermophilus, B. alkalophilus, B. amyloliquefaciens, B. coagulans, B. lautus, B. megaterium*, and *B. thuringiensis; Streptomyces* sp., such as *S. murinus*; lactic acid bacterial species including *Lactococcus* sp., such as *L. lactis; Lactobacillus* sp. including *L. reuteri; Leuconostoc* sp.; *Pediococcus* sp.; and *Streptococcus* sp. Alternatively, strains of a Gram negative bacterial species belonging to Enterobacteriaceae, including *E. coli*, or to Pseudomonadaceae can be selected as the host organism.

A suitable yeast host organism can be selected from biotechnologically relevant yeasts species, such as, but not limited to, *Pichia* sp., *Hansenula* sp., *Kluyveromyces* sp., *Yarrowinia* sp., *Saccharomyces* sp., including *S. cerevisiae*, or a species belonging to *Schizosaccharomyces*, such as *S. pombe*. A strain of the methylotrophic yeast species *Pichia pastoris* can be used as the host organism. Alternatively, the host organism can be a *Hansenula* species. Suitable host organisms among filamentous fungi include species of *Aspergillus*, e.g., *A. niger, A. oryzae, A. tubigensis, A. awamori*, or *A. nidulans*. Alternatively, a strain of *Fusarium* sp., e.g., *Fusarium oxysporum* or *Rhizomucor* sp., such as *R. miehei*, can be used as the host organism. Other suitable yeasts include *Thermomyces* sp. and *Mucor* sp. Fungal cells may be transformed by a process involving protoplast formation and transformation of the protoplasts followed by regeneration of the cell wall in a manner known in the art. A suitable procedure for transforming *Aspergillus* host cells, for example, is described in European Patent No. 238023.

In a yet further aspect, a method of producing an alpha-amylase variant is provided, which method comprises cultivating a host cell as described above under conditions conducive to the production of the variant and recovering the variant from the cells and/or culture medium. The medium used to cultivate the cells may be any conventional medium suitable for growing the host cell in question and obtaining expression of the alpha-amylase variant. Suitable media and media components are available from commercial suppliers or may be prepared according to published recipes, e.g., as described in catalogues of the American Type Culture Collection (ATCC). Exemplary culture media include but are not limited to those for fed-batch fermentations performed in for example a three thousand liter (3,000 L) stirred tank fermentor, which was used in the examples provided infra. The media used would be that most suitable for the host cell being cultured, for example the media discussed below for culturing *Bacillus licheniformis*. The growth medium in that case can consist of corn steep solids and soy flour as sources of organic compounds, along with inorganic salts as a source of sodium, potassium, phosphate, magnesium and sulfate, as well as trace elements. Typically, a carbohydrate source such as glucose is also part of the initial medium. Once the culture has established itself and begins growing, the carbohydrate is metered into the tank to maintain the culture as is known in the art. Samples are removed from the fermentor at regular intervals to measure enzyme titer using, for example, a colorimetric assay method. The fermentation process is halted when the enzyme production rate stops increasing according to the measurements.

An alpha-amylase variant secreted from the host cells may conveniently be recovered from the culture medium by well-known procedures, including separating the cells from the medium by centrifugation or filtration, and precipitating proteinaceous components of the medium by means of a salt such as ammonium sulfate, followed by the use of chromatographic procedures such as ion exchange chromatography, affinity chromatography, or the like.

Host cells may be cultured under suitable conditions that allow expression of the alpha-amylase variant proteins. Expression of the proteins may be constitutive, such that they are continually produced, or inducible, requiring a stimulus to initiate expression. In the case of inducible expression, protein production can be initiated when required by addition of an inducer substance, e.g., dexamethasone, IPTG, or Sepharose, to the culture medium, for example. Polypeptides can also be produced recombinantly in an in vitro cell-free system, such as the TnT™ (Promega) rabbit reticulocyte system.

An alpha-amylase variant expressing host also can be cultured under aerobic conditions in the appropriate medium for the host. Shaking or a combination of agitation and aeration can be provided, with production occurring at the appropriate temperature for that host, e.g., from about 30° C. to about 75° C., depending on the needs of the host and production of the desired alpha-amylase variant. Culturing can occur from about 12 to about 100 hours or greater (and any hour value there between) or more particularly from about 24 to about 72 hours. Typically, the culture broth is at a pH of about 5.5 to about 8.0, again depending on the culture conditions needed for the host cell relative to production of the alpha-amylase variant.

4.3. Purification of Alpha-Amylases

Fermentation, separation, and concentration techniques are known in the art and conventional methods can be used in order to prepare the concentrated alpha-amylase variant containing solution. After fermentation, a fermentation broth is obtained, and the microbial cells and various suspended solids, including residual raw fermentation materials, are removed by conventional separation techniques to obtain an amylase solution. Filtration, centrifugation, microfiltration, rotary vacuum drum filtration, followed by ultra-filtration, extraction or chromatography, or the like are generally used.

It is desirable to concentrate the solution containing the alpha-amylase to optimize recovery, since the use of un-concentrated solutions requires increased incubation time to collect precipitates containing the purified alpha-amylase variant. The solution is concentrated using conventional techniques until the desired enzyme level is obtained. Concentration of the enzyme variant containing solution may be achieved by any of the techniques discussed above. In one embodiment, rotary vacuum evaporation and/or ultrafiltration is used. Alternatively, ultrafiltration can be used.

By "precipitation agent" for purposes of purification is meant a compound effective to precipitate the alpha-amylase variant from the concentrated enzyme variant solution in solid form, whatever its nature may be, i.e., crystalline, amorphous, or a blend of both. Precipitation can be performed using, for example, a metal halide precipitation agent. Metal halide precipitation agents include: alkali metal chlorides, alkali metal bromides and blends of two or more of these metal halides. The metal halide may be selected from the group consisting of sodium chloride, potassium chloride, sodium bromide, potassium bromide and blends of two or more of these metal halides. Suitable metal halides include sodium chloride and potassium chloride, particularly sodium chloride, which can further be used as a preservative.

The metal halide precipitation agent is used in an amount effective to precipitate the alpha-amylase variant. The selection of at least an effective amount and an optimum amount of metal halide effective to cause precipitation of the enzyme variant, as well as the conditions of the precipitation for maximum recovery including incubation time, pH, temperature and concentration of alpha-amylase variant, will be readily apparent to one of ordinary skill in the art after routine testing.

Generally, at least about 5% w/v (weight/volume) to about 25% w/v of metal halide is added to the concentrated enzyme variant solution, and usually at least about 8% w/v. Generally, no more than about 25% w/v of metal halide is added to the concentrated enzyme variant solution and usually no more than about 20% w/v. The optimal concentration of the metal halide precipitation agent will depend, among others, on the nature of the specific alpha-amylase variant and on its concentration in the concentrated alpha-amylase variant solution.

Another alternative to effect precipitation of the enzyme is to use of organic compounds, which can be added to the concentrated enzyme variant solution. The organic compound precipitating agent can include: 4-hydroxybenzoic acid, alkali metal salts of 4-hydroxybenzoic acid, alkyl esters of 4-hydroxybenzoic acid, and blends of two or more of these organic compounds. The addition of the organic compound precipitation agents can take place prior to, simultaneously with or subsequent to the addition of the metal halide precipitation agent, and the addition of both precipitation agents, organic compound and metal halide, may be carried out sequentially or simultaneously. For a further description, see e.g., U.S. Pat. No. 5,281,526 (Danisco US Inc., Genencor Division).

Generally, the organic compound precipitation agents are selected from the group consisting of alkali metal salts of 4-hydroxybenzoic acid, such as sodium or potassium salts, and linear or branched alkyl esters of 4-hydroxybenzoic acid, wherein the alkyl group contains from 1 to 12 carbon atoms, and blends of two or more of these organic compounds. The organic compound precipitations agents can be for example linear or branched alkyl esters of 4-hydroxybenzoic acid, wherein the alkyl group contains from 1 to 10 carbon atoms, and blends of two or more of these organic compounds. Suitable organic compounds include linear alkyl esters of 4-hydroxybenzoic acid, wherein the alkyl group contains from 1 to 6 carbon atoms, and blends of two or more of these organic compounds. Methyl esters of 4-hydroxybenzoic acid, propyl ester of 4-hydroxybenzoic acid, butyl ester of 4-hydroxybenzoic acid, ethyl ester of 4-hydroxybenzoic acid and blends of two or more of these organic compounds can also be used. Additional organic compounds also include, but are not limited to, 4-hydroxybenzoic acid methyl ester (methyl PARABEN) and 4-hydroxybenzoic acid propyl ester (propyl PARABEN), which are also amylase preservative agents.

Addition of the organic compound precipitation agent provides the advantage of high flexibility of the precipitation conditions with respect to pH, temperature, alpha-amylase variant concentration, precipitation agent concentration, and time of incubation.

The organic compound precipitation agent is used in an amount effective to improve precipitation of the enzyme variant by means of the metal halide precipitation agent. The selection of at least an effective amount and an optimum amount of organic compound precipitation agent, as well as the conditions of the precipitation for maximum recovery including incubation time, pH, temperature and concentration of enzyme variant, will be readily apparent to one of ordinary skill in the art, in light of the present disclosure, after routine testing.

Generally, at least about 0.01% w/v of organic compound precipitation agent is added to the concentrated enzyme variant solution and usually at least about 0.02% w/v. Generally, no more than about 0.3% w/v of organic compound precipitation agent is added to the concentrated enzyme variant solution and usually no more than about 0.2% w/v.

The concentrated enzyme variant solution, containing the metal halide precipitation agent and, in one aspect, the organic compound precipitation agent, is adjusted to a pH that necessarily will depend on the enzyme variant to be purified. Generally, the pH is adjusted to a level near the isoelectric point (pI) of the amylase. For example, the pH can be adjusted within a range of about 2.5 pH units below the pI to about 2.5 pH units above the pI. For purposes of illustration, when the alpha-amylase variant is derived from *B. licheniformis*, the concentrated enzyme variant solution is usually adjusted to a pH of between about 5.5 and 9.7 and particularly to a pH of between about 6.5 and 9.0. The pH may be adjusted accordingly if the pI of the variant differs from the wild-type pI.

The incubation time necessary to obtain a purified enzyme variant precipitate depends on the nature of the specific enzyme variant, the concentration of enzyme, and the specific precipitation agent(s) and its (their) concentration. Generally, the time effective to precipitate the enzyme variant is between about 1 to about 30 hours; usually it does not exceed about 25 hours. In the presence of the organic compound precipitation agent, the time of incubation can still be reduced to less than about 10 hours, and in most cases even about 6 hours.

Generally, the temperature during incubation is between about 4° C. and about 50° C. Usually, the method is carried out at a temperature between about 10° C. and about 45° C., and particularly between about 20° C. and about 40° C. The optimal temperature for inducing precipitation varies according to the solution conditions and the enzyme variant or precipitation agent(s) used.

The overall recovery of purified enzyme variant precipitate, and the efficiency with which the process is conducted, is improved by agitating the solution comprising the enzyme variant, the added metal halide and the added organic compound. The agitation step is done both during addition of the metal halide and the organic compound, and during the subsequent incubation period. Suitable agitation methods include mechanical stirring or shaking, vigorous aeration, or any similar technique.

After the incubation period, the purified enzyme variant is then separated from the dissociated pigment and other impurities and collected by conventional separation techniques, such as filtration, centrifugation, microfiltration, rotary vacuum filtration, ultrafiltration, press filtration, cross membrane microfiltration, cross flow membrane microfiltration or the like. Cross membrane microfiltration can be one method used. Further purification of the purified enzyme variant precipitate can be obtained by washing the precipitate with water. For example, the purified enzyme variant precipitate is washed with water containing the metal halide precipitation agent, for example, with water containing the metal halide and the organic compound precipitation agents.

During the culturing, thermostable amylase extracellularly accumulates in the culture broth. For the isolation and purification of the desired alpha-amylase variant, the culture broth is centrifuged or filtered to eliminate cells, and the resulting cell-free liquid is used for the purification of the enzyme. In one embodiment, the cell-free broth is subjected to salting out using ammonium sulfate at about 70% saturation; the 70% saturation-precipitation fraction is then dissolved in a buffer and applied to a column such as a Sephadex G-100 column, and eluted to recover the enzyme variant active fraction. For further purification, a conventional procedure such as ion exchange chromatography may be used.

Purified enzyme variants are useful for all applications in which the enzyme variants are generally utilized. For example, they can be used in laundry detergents and spot removers, in the food industry, in starch processing and baking, and in pharmaceutical compositions as digestive aids. They can be made into a final product that is either liquid (solution, slurry) or solid (granular, powder).

Alternatively, the enzyme product can be recovered and a flocculating agent is added to the media in order to remove cells and cell debris by filtration or centrifugation without further purification of the enzyme.

5. Other Enzymes Used in Starch Processing 5.1. Glucoamylases

Another enzyme contemplated for use in the starch processing, especially during saccharification, is a glucoamylase (EC 3.2.1.3). Glucoamylases are commonly derived from a microorganism or a plant. For example, glucoamylases can be of fungal or bacterial origin.

Exemplary fungal glucoamylases are *Aspergillus* glucoamylases, in particular *A. niger* G1 or G2 glucoamylase (Boel et al., *EMBO J.* 3(5): 1097-1102 (1984)), or variants thereof, such as disclosed in WO 92/00381 and WO 00/04136; *A. awamori* glucoamylase (WO 84/02921); *A. oryzae* glucoamylase (Hata et al., *Agric. Biol. Chem.*, 55(4): 941-949 (1991)), or variants or fragments thereof. Other contemplated *Aspergillus* glucoamylase variants include variants with enhanced thermal stability: G137A and G139A (Chen et al., *Prot. Eng.* 9: 499-505 (1996)); D257E and D293E/Q (Chen et al., *Prot. Eng.* 8: 575-582 (1995)); N182 (Chen et al., *Biochem. J.* 301: 275-281 (1994)); disulphide bonds, A246C (Fierobe et al., Biochemistry, 35: 8698-8704 (1996)); and introduction of Pro residues in positions A435 and S436 (Li et al., *Protein Eng.* 10: 1199-1204 (1997)).

Exemplary fungal glucoamylases may also include *Trichoderma reesei* glucoamylase and its homologs as disclosed in U.S. Pat. No. 7,413,879 (Danisco US Inc., Genencor Division). These glucoamylases include *Trichoderma reesei* glucoamylase (SEQ ID NO: 4), *Hypocrea citrina* var. *americana* glucoamylase (SEQ ID NO: 6), *Hypocrea vinosa* glucoamylase (SEQ ID NO: 8), *Trichoderma* sp. glucoamylase (SEQ ID NO: 10), *Hypocrea gelatinosa* glucoamylase (SEQ ID NO: 12), *Hypocrea orientalis* glucoamylase (SEQ ID NO: 14), *Trichoderma konilangbra* glucoamylase (SEQ ID NO: 16), *Trichoderma* sp. glucoamylase (SEQ ID NO: 29), *Trichoderma harzianum* glucoamylase (SEQ ID NO: 31), *Trichoderma longibrachiatum* glucoamylase (SEQ ID NO: 33), *Trichoderma asperellum* glucoamylase (SEQ ID NO: 35), and *Trichoderma strictipilis* glucoamylase (SEQ ID NO: 37).

Other contemplated glucoamylases include *Talaromyces* glucoamylases, in particular derived from *T. emersonii* (WO 99/28448), *T. leycettanus* (U.S. Pat. No. RE 32,153), *T. duponti*, or *T. thermophilus* (U.S. Pat. No. 4,587,215). Contemplated bacterial glucoamylases include glucoamylases from the genus *Clostridium*, in particular *C. thermoamylolyticum* (EP 135138) and *C. thermohydrosulfuricum* (WO 86/01831).

Suitable glucoamylases include the glucoamylases derived from *Aspergillus oryzae*, such as a glucoamylase having about 50%, about 55%, about 60%, about 65%, about 70%, about 75%, about 80%, about 85%, or even about 90% identity to the amino acid sequence shown in SEQ ID NO: 2 in WO 00/04136. Suitable glucoamylases may also include the glucoamylases derived from *Trichoderma reesei*, such as a glucoamylase having about 50%, about 55%, about 60%, about 65%, about 70%, about 75%, about 80%, about 85%, or even about 90% identity to the amino acid sequence shown in SEQ ID NO: 1 or 3 in WO 08/045,489 (Danisco US Inc., Genencor Division). *Trichoderma reesei* glucoamylase variants with altered properties, such as those disclosed in WO 08/045,489 and U.S. Ser. No. 12/292,563, filed Nov. 20, 2008 (Danisco US Inc., Genencor Division), may be particularly useful.

Also suitable are commercial glucoamylases, such as Spirizyme® Fuel, Spirizyme® Plus, and Spirizyme® Ultra (Novozymes A/S, Denmark), G-ZYME® 480, G-ZYME® 480 Ethanol, GC 147, DISTILLASE®, and FERMENZYME® (Danisco US Inc., Genencor Division). Glucoamylases may be added in an amount of 0.02-2.0 AGU/g ds or 0.1-1.0 AGU/g ds, e.g., 0.2 AGU/g ds.

5.2. Pullulanase

Pullulanases (E.C. 3.2.1.41) are debranching enzymes characterized by their ability to hydrolyze the α-1,6-glycosidic bonds in, for example, amylopectin and pullulan. Pullulanases have been found useful in various industrial applications, particularly in the food and beverage industries. Pullulanases are starch debranching enzymes and are effective in the debranching of starch hydrolysates (useful in conditioning dough), the debranching of beta-limit dextrans (useful in the brewing of beer and ales), and in the production of sugar syrups from starch-containing materials, such as corn, potato, wheat, manioc, and rice.

Pullulanase activity may be measured with the reducing sugars method as described in U.S. Pat. No. 5,736,375, which is incorporated herein by reference. See also, Nelson N., "A Photometric Adaptation of the Somogyi Method for the Determination of Glucose," *J. Biol. Chem.* 153: 375-80 (1944); Somogyi M., "A New Reagent for the Determination of Sugars," *J. Biol. Chem.* 160: 61-68 (1945).

Representative pullulanases include those from the genus *Bacillus*, particularly the pullulanase from *Bacillus amyloderamificans* as disclosed in U.S. Pat. No. 4,560,651, the pullulanase disclosed as SEQ ID NO: 2 in WO 01/051620, the pullulanase from *Bacillus deramificans* disclosed as SEQ ID NO: 4 in WO 01/051620, and the pullulanase from *Bacillus acidopullulyticus* disclosed as SEQ ID NO: 6 in WO 01/051620, all of which are incorporated herein by reference. See also, Kelly et al., "Molecular Genetic analysis of the Pullulanase B Gene of *Bacillus acidopullulyticus*," FEMS Microbiol. Lett. 115: 97-106 (1994).

Additionally, the pullulanase may be a variant of a naturally occurring pullulanase. The production of *Bacillus deramificans* pullulanase has been described in U.S. Pat. Nos. 5,736,375 and 7,399,623, both of which are incorporated herein by reference.

Suitable commercially available pullulanases include PROMOZYME D, PROMOZYME™ D2 (Novozymes A/S), OPTIMAX L-300 (Danisco US Inc., Genencor Division), KLEISTASE PL45 and KLEISTASE PLF (Aman Enzyme Inc., Japan).

5.3. Glucose Isomerases

Commercial glucose isomerase is actually a xylose isomerase (D-xylose ketol isomerase, EC 5.3.1.5), an intracellular enzyme that catalyzes the isomerization of D-xylose to D-xylulose. However, the practical significance of the enzyme stems from the fact that the xylose isomerase can use either D-xylose or D-glucose as substrates. The enzyme's commercial use is mainly for high fructose syrup production. See Kaneko et al., *Biosci. Biotechnol. Biochem.* 64:940-947 (2000)). At present, the commercial glucose isomerases come mainly from *Actinoplanes missouriensis*, *Bacillus coagulans*, or *Streptomyces* species. Contemplated isomerases included the commercial products Sweetzyme®, IT (Novozymes A/S); GENSWEET® IGI SA, GENSWEET® IGI HF, GENSWEET® IGI VHF, GENSWEET® SGI, and GENSWEET® IGI MAX (Danisco US Inc., Genencor Division).

5.4. Phytases

Phytases are useful for the present disclosure as they are capable of hydrolyzing phytic acid under the defined conditions of the incubation and liquefaction steps. In some embodiments, the phytase is capable of liberating at least one inorganic phosphate from an inositol hexaphosphate (phytic acid). Phytases can be grouped according to their preference for a specific position of the phosphate ester group on the phytate molecule at which hydrolysis is initiated (e.g., as 3-phytases (EC 3.1.3.8) or as 6-phytases (EC 3.1.3.26)). A typical example of phytase is myo-inositol-hexakisphosphate-3-phosphohydrolase.

Phytases can be obtained from microorganisms such as fungal and/or bacterial organisms. Some of these microorganisms include e.g. *Aspergillus* (e.g., *A. niger*, *A. terreus*, *A. ficum* and *A. fumigatus*), *Myceliophthora* (*M. thermophila*), *Talaromyces* (*T. thermophilus*) *Trichoderma* spp (*T. reesei*). and *Thermomyces* (WO 99/49740). Phytases are also available from *Penicillium* species, e.g., *P. hordei* (ATCC No. 22053), *P. piceum* (ATCC No. 10519), or *P. brevi-compactum* (ATCC No. 48944). See, e.g., U.S. Pat. No. 6,475,762. In addition, phytases are available from *Bacillus* (e.g., *B. subtilis*, *Pseudomonas*, *Peniophora*, *E. coli*, *Citrobacter*, *Enterbacter*, and *Buttiauxella* (see WO2006/043178)).

Commercial phytases are available such as NATUPHOS (BASF), RONOZYME P (Novozymes A/S), and FINASE (AB Enzymes). The method for determining microbial phytase activity and the definition of a phytase unit has been published by Engelen et al., *J. of AOAC Int.*, 77: 760-764 (1994). The phytase may be a naturally occurring phytase, a variant, or a fragment thereof.

In one embodiment, the phytase is one derived from the bacterium *Buttiauxiella* spp. The *Buttiauxiella* spp. includes *B. agrestis*, *B. brennerae*, *B. ferragutiase*, *B. gaviniae*, *B. izardii*, *B. noackiae*, and *B. warmboldiae*. Strains of *Buttiauxella* species are available from DSMZ, the German National Resource Center for Biological Material (Inhoffenstrabe 7B, 38124 Braunschweig, Germany). *Buttiauxella* sp. strain P1-29 deposited under accession number NCIMB 41248 is an example of a particularly useful strain from which a phytase may be obtained and used according to the present disclosure. In some embodiments, the phytase is BP-wildtype, a variant thereof (such as BP-11) disclosed in WO 06/043178, or a variant as disclosed in US 2008/0220498, published Sep. 11, 2008. For example, a BP-wild-type and variants thereof are disclosed in Table 1 of WO 06/043178, wherein the numbering is in reference to SEQ ID NO: 3 of the published PCT application.

5.5. Beta-Amylase

Another aspect contemplates the additional use of a beta-amylase. Beta-amylases (EC 3.2.1.2) are exo-acting maltogenic amylases, which catalyze the hydrolysis of 1,4-α-glucosidic linkages into amylose, amylopectin, and related glucose polymers, thereby releasing maltose. Beta-amylases have been isolated from various plants and microorganisms (Fogarty et al., PROGRESS IN INDUSTRIAL MICROBIOLOGY, Vol. 15, pp. 112-115, 1979). These beta-amylases are characterized by having optimum temperatures in the range from 40° C. to 65° C., and optimum pH in the range from about 4.5 to about 7.0. Contemplated β-amylases include, but are not limited to, beta-amylases from barley SPEZYME® BBA 1500, SPEZYME® DBA, OPTIMALT™ ME, OPTIMALT™ BBA (Danisco US Inc, Genencor Division); and Novozym™ WBA (Novozymes A/S).

EXAMPLES

The following examples are not to be interpreted as limiting, but are exemplary means of using the methods disclosed.

Materials and Methods

Fuelzyme®-LF

Commercial product of Fuelzyme®-LF (lot #90BA031A1M1 activity 134,603 MWU/g) was provided by Brian A. Steer, Ph.D., Fuelzyme®-LF Product Manager, Verenium Corporation, 4955 Directors Place, San Diego, Calif. 92121, Tel: 858-526-5264, Fax: 858-526-5764.

SPEZYME® FRED and OPTIMAX® 4060 VHP

SPEZYME® FRED and OPTIMAX® 4060 VHP were from Danisco US Inc., Genencor Division (lot #1077061001; activity 17662 AAUs/g).

Bradford Assay for Protein Content Determination in 96-Well Microtiter Plate

Protein concentration in sample supernatants was determined using the Bradford QuickStart™ Dye Reagent (Bio-Rad, California). Samples were obtained by filtration of broths from cultures grown in microtiter plates (MTPs). The cultures were grown for 3 days at 37° C. with shaking at 280 rpm and humidified aeration. A 10 μL sample of the culture filtrate was combined with 200 μL Bradford QuickStart™ Dye Reagent in a well of a second MTP. After thorough mixing, the MTP's were incubated for at least 10 minutes at room temperature. Air bubbles were removed, and the OD (optical density) was measured at 595 nm. To determine the protein concentration, the background reading (from uninoculated wells) was subtracted from the sample readings.

Sediment Test

All starches, especially grain-based, contain traces of components other than dextrose polymers such as fine fiber, proteins, fats, and ash that are released during hydrolysis. The starch cooking parameters and operating equipment such as the steam jet cooker has a bearing on the quantity of this material. Small amounts of starch-lipid complexes and under the right conditions, partially pasted and/or whole starch granules may pass through the liquefaction system. Due to incomplete hydrolysis in the liquefaction system, the most reliable location to test for these components is after complete saccharification. A well run liquefaction system that is receiving well-washed starch from the milling division should test at <1.5% sediment by this method. There are systems that consistently deliver <1%. Operating history has shown that sediment levels above 2.5% will result in down stream filtration difficulties, and thus costs for pre-coat media and/or microfilters.

This method described herein may be used for all dextrose substrates >90% dextrose. This may also be used for maltose liquors, and liquefied low DE products. Due to viscosity and buoyant force issues caused by final saccharified dry substances >5%, liquors known to be greater than this should be diluted prior to testing.

Samples of saccharified syrup were held in a 60° C. water bath for 10-30 minutes to bring them to a constant temperature. The incubation, however, should not be longer than one hour. The DS value was adjusted to 35%±0.5% prior to testing as necessary. Samples were mixed on a magnetic stirrer, and transferred to a centrifuge tube using a syringe. Samples were centrifuged at 2,500 rpm (1,350×g) for 10 minutes. The sediment, if present, was visible at the bottom of the centrifuge tube.

Filtration Test

This test is based on the filtration rate through a controlled depth of filter aid (diatomaceous earth) under controlled temperature and vacuum. This test can identify differences in liquefaction enzymes and processes, following saccharification. This test is suitable for the simulation of industrial rotary vacuum pre-coat filtration systems. It may be used for determination and demonstration of various liquefaction and saccharification enzymes and processes. In addition, the filtrate provides clean material for further evaluation such as the determination of soluble starch with iodine reaction.

Column jackets were maintained at 60° C. Two filter paper discs were inserted and screwed in the fitting until snug against the O-ring gasket. While a tared 250 ml vacuum flask was in place, 100 ml of water was added to the column with the exit plugged. The vacuum pump was turned on until a steady vacuum of 23-24 inches was achieved. The tube exit was turned on, and a timer was started. The 100 ml takes about 1 min 10 seconds to 1 min 30 seconds to filter through the system. If not, then check the papers to make sure they are tight. After the papers were pulled to dryness, the exit tube was clamped. The pump was left running with the clamp removed from the exit tube. The flask was replaced with a tared 250 ml filter flask. Approximately 2.0 grams of filter aid was mixed with 100 grams of test liquor in a 250 ml beaker. While the sample was stirring on the magnetic plate, a syringe was used to remove the sample with targeted quantity. A top loading balance may be used for this step. While keeping the particulates in suspension, the entire quantity was rapidly transferred to the column with the aid of a funnel. The exit tube clamp was turned on, and a timer was started. Collect until the liquor reaches the top of the filter bed and record the time. The quantity of filtrate across multiple tests may be used to judge operating differences in liquefaction or saccharification. Alternatively, the rate may be calculated in weight or volume per square meter of filter bed.

For example, 60 grams of filtrated was collected in 15 minutes. The area of filter bed surface is calculated as $\pi r^2$, in this case $3.141593 \times 0.75 \times 0.75 = 1.767$ cm$^2$ (the column has an inner radius of 0.75 cm). In addition, the 60 grams of filtrate was equivalent to 52 ml of the sample, which has a 35% DS and a density of 1.151 g/mL. The filtrate rate is thus 52 ml/1.767 cm$^2$/15 min=1.96 ml/cm$^2$/min Iodine Test For saccharification liquor test, 0.2 ml saccharification liquor was diluted with 10 ml of DI water. The diluted saccharification liquor was boiled for 10 minutes and then cooled in an ice bath. 0.5 ml iodine solution (0.02 M) was added to the cooled saccharification liquor sample.

For filtrate test, 0.5 ml filtrate, which was obtained as described in Example 1.3., was diluted with 10 ml of DI water. The diluted filtrate was boiled for 10 minutes and cooled in an ice bath. 0.5 ml iodine solution (0.02 M) was added to the cooled filtrate sample.

HPLC Method to Measure the Composition of Glucose Syrup

The composition of saccharification products was measured by a HPLC system (Beckman System Gold 32 Karat Fullerton, Calif.). The system, maintained at 50° C., was equipped with a Rezex 8 u8% H Monosaccharides column and a refractive index (RI) detector (ERC-7515A, Anspec Company, Inc.). Diluted sulfuric acid (0.01 N) was applied as the mobile phase at a flow rate of 0.6 ml/min. 20 µl of 4.0% solution of the reaction mixture was injected onto the column. Elution profiles were obtained over 45 minutes. The distribution of saccharides and the amount of each saccharide were determined from previously run standards.

Example 1

Comparison of Fuelzyme®-LF and SPEZYME® FRED

A 38% DS refined starch (Cargill, Minneapolis, Minn.) slurry containing 10 ppm $Ca^{2+}$ and 100 ppm sulfur dioxide ($SO_2$) was prepared in a metal bucket with overnight stirring. The pH of the slurry was adjusted to pH 4.5, 5.6, and 5.8 using sodium carbonate solution (20% w/v). The slurry Baumé (degrees) was approximately 22.3. Three sets of liquefactions were performed with Fuelzyme®-LF at different enzyme dosages and specified pHs, and one set was performed with SPEZYME® FRED. The liquefaction was carried out as follows: (1) Fuelzyme®-LF at 50 MWUs/g ds at pH 4.5, (2) Fuelzyme®-LF at 50 MWUs/g ds at pH 5.6, (3) Fuelzyme®-LF at 25 MWUs/g ds at pH 5.6, and (4) SPEZYME® FRED at 10 LUs/g ds at pH 5.8.

The slurry with the enzyme(s) added was sent through a pilot plant jet cooker (Hydro-thermal Corporation, Waukesha, Wis.) at 0.5 gpm with six-minute residence time and cooked at about 108-110° C. for the primary cook. Secondary liquefaction was performed at 95° C. for 120 minutes. The DE and refractive index (RI) were measured at various time points during the secondary liquefaction (Table 1A).

TABLE 1A

DE development for Fuelzyme ®-LF and SPEZYME ® FRED

| Enzyme Treatment | Time min. | D.E. |
| --- | --- | --- |
| Fuelzyme ®-LF at 50 MWUs/g ds at pH 4.5 | 30 | 7.38 |
|  | 60 | 10.21 |
|  | 66 | 11.72 |
| Fuelzyme ®-LF at 25 MWUs/g ds at pH 5.6 | 30 | 3.66 |
|  | 60 | 5.74 |
|  | 90 | 7.34 |
|  | 132 | 8.79 |
| Fuelzyme ®-LF at 50 MWUs/g ds at pH 5.6 | 30 | 7.74 |
|  | 60 | 10.48 |
|  | 90 | 12.47 |
|  | 120 | 13.88 |
| SPEZYME ® FRED at 10 LUs/g ds pH 5.8 | 30 | 4.59 |
|  | 60 | 7.29 |
|  | 90 | 9.59 |
|  | 103 | 10.57 |

The data in Table 1A show that the DE development during the secondary liquefaction. Liquefaction with Fuelzyme®-LF with a dose of 50 MWUs/g ds at both pH 4.5 and 5.6 was able to generate 10 DE in 60 min. Whereas, Fuelzyme®-LF with 25 MWUs/g ds was not able to generate 10 DE even at 132 min. This result shows that the DE development rate in secondary liquefaction was almost doubled by doubling the Fuelzyme®-LF dosage as Fuelzyme®-LF achieved 10 DE in half the time with 50 MWUs compared to 25 MWUs. The secondary liquefaction with SPEZYME® FRED generated 10.57 DE in 103 min, which is a standard DE development rate with SPEZYME® FRED under used conditions.

The pH of the liquefact was adjusted to pH 4.2 and the DS was adjusted to 34% DS. The saccharification enzyme blend OPTIMAX® 4060 VHP was added at 0.16 GAUs/g ds. The saccharification was carried out at 60° C. for 48-64 hours. At various time points, samples were taken and the composition of the reaction products were determined by the HPLC method (Table 1B).

TABLE 1B

High glucose syrup composition using liquefied starch from different liquefying enzyme combinations.

| Liquefying Enzymes | DPs | 24 hr | 48 hr |
| --- | --- | --- | --- |
| Fuelzyme ®-LF at 50 MWUs/g ds at pH 4.5 | DP1 | 94.06 | 95.74 |
|  | DP2 | 1.64 | 1.90 |
|  | DP3 | 0.85 | 2.36 |
| Fuelzyme ®-LF at 25 MWUs/g ds at pH 5.6 | DP1 | 91.38 | 94.515 |
|  | DP2 | 2.482 | 2.518 |
|  | DP3 | 3.939 | 1.98 |
| Fuelzyme ®-LF at 50 MWUs/g ds at pH 5.6 | DP1 | 92.74 | 94.95 |
|  | DP2 | 2.32 | 2.92 |
|  | DP3 | 4.94 | 2.14 |
| SPEZYME ® FRED at 10 LUs/g ds pH 5.8 | DP1 | 90.82 | 95.35 |
|  | DP2 | 2.48 | 2.82 |
|  | DP3 | 3.61 | 1.11 |

After the saccharification, the glucose syrup was tested for (1) iodine test (Materials and Methods), (2) sediment test (Materials and Methods), and (3) filtration test (Materials and Methods). The values were compiled in Table 1C.

TABLE 1C

The blue saccharide, sediment, filtration, and glucose results for the saccharification liquor from Fuelzyme ®-LF and SPEZYME ® FRED liquefact.

| Enzyme | pH | Sediment % | Filter g/ 15 min | Iodine Color |
| --- | --- | --- | --- | --- |
| Fuelzyme ®-LF at 50 MWUs/g ds | 4.5 | 5 | 17 | Blue |
| Fuelzyme ®-LF at 25 MWUs/g ds | 5.6 | 15 | 11.22 | Blue |
| Fuelzyme ®-LF at 50 MWUs/g ds | 5.6 | 3 (Firm) | 33.5 | Blue |
| SPEZYME ® FRED at 10 LUs/g ds | 5.8 | 0.5 | 67 | Yellow |

Due to incomplete hydrolysis of starch in the liquefaction system, the high glucose level observed at the end of the saccharification does not necessarily indicate that the saccharified starch is suitable for sweetener application. One of the most reliable methods is the iodine-positive saccharide (IPS; or blue saccharide) measured by the iodine test. The saccharified starch was subject to iodine test for both the filtrate and the sediments. Iodine is able to bind any amylose that escapes hydrolysis during liquefaction/saccharification and produce a blue color, which is termed iodine-positive saccharide. IPS is highly undesirable in sweetener applications. Both the sediment and the filtrate of the saccharified starch were subject to iodine test.

Also, the sediment test was performed after the saccharification. Incompletely hydrolyzed starch may be complexed with lipid, protein, and/or fine fiber to form sediments in the glucose syrup. A high level of sediments is undesirable for sweetener applications, because the sediments may substantially reduce filtration rate requiring addition of high level of filter aid resulting in higher cost and disposal problems. This will also reduce the plant capacity. A well-run liquefaction system that is receiving well-washed starch from the milling division generally results in sediment less than 1.5% v/v.

The high glucose syrup obtained using liquefact from Fuelzyme®-LF exhibited an iodine-positive saccharide (IPS). When stained with iodine, the sediment and filtrate turned blue/green color (FIG. 1) indicating that amylose (DP>46-54) is still present after saccharification for liquefact obtained from Fuelzyme®-LF. The liquefact is thus unacceptable for sweetener applications. The high glucose syrup obtained using liquefact from Fuelzyme®-LF also exhibited high level of sediments. Both results are undesirable for the production of HFCS (high fructose corn syrup).

The sediment or filtrate obtained from high glucose syrup using SPEZYME® FRED liquefact did not exhibit blue color when stained with iodine and turned yellow (FIG. 1), and showed lower level (<1.5%) of sediments, which is ideal in the production of HFCS.

Moreover, another reliable method to evaluate a saccharified starch is the filtration test, which is similar to the sediment test. The filtration rate is inversely affected by the amount of sediments. The filtration test results are compatible with what was observed in sediment test. See Table 1C. The saccharified starch from the various Fuelzyme®-LF liquefact exhibited a low filtration rate, ranging from 11 to 33.5 g/15 min. Whereas, for the saccharified starch from the liquefact by SPEZYME® FRED, the filtration rate improved to 67 g/15 min, which is twice the rates of the Fuelzyme®-LF liquefact.

To fully realize the potential of this low pH, thermostable enzyme in sweetener applications, a blend combining Fuelzyme®-LF and a *Bacillus licheniformis* alpha-amylase was tested to overcome the blue saccharide or IPS problems associated with Fuelzyme®-LF in sweetener production and is explained in following examples.

Example 2

Fuelzyme®-LF and SPEZYME® FRED Blend in Starch Liquefaction

Aqueous slurry containing 38% DS refined starch (Cargill, Minneapolis, Minn.), 10 ppm $Ca^{2+}$, and 100 ppm sulfur dioxide ($SO_2$) was prepared by stirring overnight. The pH of the slurry was adjusted using sodium carbonate solution (20% w/v). The Baumé (degrees) of the slurry were approximately 22.3. Single set of liquefaction was performed using 25 MWUs/g ds Fuelzyme®-LF supplemented with 5 LUs/g ds of SPEZYME® FRED at pH 5.6. The slurry with the enzyme(s) added was sent through the big jet at 0.5 gpm with six-minute residence time and cooked at about 108-110° C. for the primary cook. Secondary liquefaction was performed at 95° C. for 120 minutes. The DE and refractive index (RI) were measured at various time points during the secondary liquefaction. Table 2A reflects the DE values determined at various time of secondary liquefaction for the two sets of liquefaction. The results indicate that at pH 5.6, the Fuelzyme®-LF/SPEZYME® FRED 25/5 blend is able to achieve DE development that is acceptable for starch liquefaction in sweetener applications, i.e., a DE value of at least 10 in 90-100 min. The data presented herewith suggest that the DE development during liquefaction by the Fuelzyme®-LF/SPEZYME® FRED, 25/5 blend at pH 5.6 is compatible with the industrial standard.

TABLE 2A

DE development for Fuelzyme ®-LF/SPEZYME ® FRED blend at pH 5.6 and 5.3

| Enzyme Treatment | Time min. | D.E. |
|---|---|---|
| Fuelzyme ®-LF/SPEZYME ® FRED 25/5 blend at pH 5.6 | 30 | 5.53 |
| | 60 | 8.47 |
| | 90 | 10.66 |
| | 120 | 12.47 |

Next, the suitability of the resulting liquefact in sweetener applications was tested in the saccharification. The liquefact was adjusted to pH 4.2 and 34% DS. Saccharification enzyme OPTIMAX® 4060 VHP was added at 0.16 GAUs/g ds. The saccharification was carried at 60° C. for 48-64 hours. At various time points, samples were taken and the composition of the reaction products were determined by the HPLC method (Table 2B). As shown in Table 2B, glucose production reached approximately 95% in 48 hrs for the liquefact by Fuelzyme®-LF/SPEZYME® FRED Blend, 25/5 blend. The glucose production level is similar to that achieved from the liquefact by Fuelzyme®-LF in Example 1.

TABLE 2B

High glucose syrup composition using liquefied starch from different liquefying enzyme combinations.

| Liquefying Enzymes | DPs | 5 hr | 19 hr | 29 hr | 41 hr | 48 hr | 64 hr |
|---|---|---|---|---|---|---|---|
| Fuelzyme ®-LF + | DP1 | 52.52 | 90.41 | 93.45 | 94.78 | 94.97 | 95.30 |
| SPEZYME ® FRED Blend | DP2 | 13.01 | 2.60 | 2.29 | 2.48 | 2.52 | 2.86 |
| pH 5.6 | DP3 | | 3.90 | 2.88 | 1.86 | 1.69 | 1.15 |

The saccharified starch was further evaluated by (1) iodine test, (2) sediment test, and (3) filtration test (as previously discussed), all of which are used to evaluate the potential of converting the saccharified starch (glucose syrup) to the high fructose syrup (HFCS or HFSS).

The saccharified starch (glucose syrup) was subject to iodine test for both the filtrate and the sediments. See FIG. 1. When stained with iodine, the sediment from saccharified starch originally liquefied with Fuelzyme®-LF/SPEZYME® FRED Blend 25/5, turned yellow. This result indicated the absence of amylose complex after saccharification. The corresponding liquefact is of acceptable quality for sweetener applications. When the filtrate was subject to iodine test, the sample developed a yellow color giving similar results as in sediment iodine test. The saccharified starch achieved from Fuelzyme®-LF/SPEZYME® FRED blend was subject to the sediment test and the result is shown in Table 2C. The saccharified starch from the liquefact by Fuelzyme®-LF/SPEZYME® FRED blend 25/5 blend showed only 0.5% sediment, which is well below the 1.5% industrial threshold and satisfactory for industrial usage.

The filtration result was also compatible with what was observed in sediment test. See Table 2C. The saccharified starch from the liquefact by Fuelzyme®-LF/SPEZYME® FRED Blend exhibited the filtration rate improvement to 83 g/15 min, which is more than 2.5 times of the rates of the previous results from Fuelzyme®-LF in Example 1.

TABLE 2C

The blue saccharide, sediment, filtration and glucose results for the saccharification liquor from Fuelzyme ®-LF/SPEZYME ® FRED blend

| Enzyme | pH | Sediment % | Filter g/ 15 min | Iodine Color |
|---|---|---|---|---|
| Fuelzyme ®-LF + SPEZYME ® FRED Blend | 5.6 | 0.5 | 83 | Neg/ yellow |

Example 3

The starch slurry containing 38% DS refined starch (Cargill, Minneapolis, Minn.), containing 10 ppm $Ca^{2+}$, and 100 ppm sulfur dioxide ($SO_2$) was prepared in a metal bucket with overnight stirring. The pH of the slurry was adjusted to pH 5.6 using sodium carbonate solution (20% w/v). The slurry Baumé (degrees) was approximately 22.3. Four sets of liquefactions were performed which included constant dose of Fuelzyme®-LF and varying dose of SPEZYME® FRED. The liquefaction was carried out as follows:

(1) Fuelzyme®-LF at 25 MWUs/g and SPEZYME® FRED at 5 LUs/g;

(2) Fuelzyme®-LF at 25 MWUs/g and SPEZYME® FRED at 2.5 LUs/g;

(3) Fuelzyme®-LF at 25 MWUs/g and SPEZYME® FRED at 1 LUs/g; and (4) Fuelzyme®-LF at 25 MWUs/g The slurry with the enzyme(s) added was sent through a pilot plant jet cooker (Hydro-thermal Corporation, Waukesha, Wis.) at 0.5 gpm with six-minute residence time and cooked at about 108-110° C. for the primary cook. Secondary liquefaction was performed at 95° C. for 120 minutes. The DE and refractive index (RI) were measured at various time points during the secondary liquefaction.

The data in Table 3A shows the DE development during the secondary liquefaction. The DE progressions were as expected through the enzyme dosages and were highest for the liquefaction 1 followed by liquefaction 2, liquefaction 3, and liquefaction 4 respectively.

TABLE 3A

DE development for Fuelzyme ®-LF and SPEZYME ® FRED

| Enzyme Treatment | Time min. | D.E. |
|---|---|---|
| Fuelzyme ®-LF at 25 MWUs/g and SPEZYME ® FRED at 5 LUs/g | 30 | 6.35 |
|  | 60 | 8.75 |
|  | 82 | 10.29 |
| Fuelzyme ®-LF at 25 MWUs/g and SPEZYME ® FRED at 2.5 LUs/g | 30 | 4.92 |
|  | 60 | 7.05 |
|  | 102 | 9.89 |
| Fuelzyme ®-LF at 25 MWUs/g and | 30 | 3.65 |

TABLE 3A-continued

DE development for Fuelzyme ®-LF and SPEZYME ® FRED

| Enzyme Treatment | Time min. | D.E. |
|---|---|---|
| SPEZYME ® FRED at 1 LUs/g | 60 | 6.05 |
|  | 90 | 7.74 |
|  | 125 | 9.18 |
| Fuelzyme ®-LF at 25 MWUs/g and SPEZYME ® FRED at 0 LUs/g | 30 | 3.66 |
|  | 60 | 5.74 |
|  | 90 | 7.34 |
|  | 132 | 8.79 |

The saccharification performances were similar for all the treatment with glucose levels reaching ~94-95% in 48 hrs (Table 3B).

TABLE 3B

High glucose syrup composition using liquefied starch from different liquefying enzyme combinations.

| Enzyme Treatment | Hour | DP1 | DP2 | DP3 |
|---|---|---|---|---|
| Fuelzyme ®-LF at 25 MWUs/g and SPEZYME ® FRED at 5 LUs/g | 24 | 90.109 | 2.939 | 4.609 |
|  | 48 | 94.091 | 2.468 | 2.481 |
| Fuelzyme ®-LF at 25 MWUs/g and SPEZYME ® FRED at 2.5 LUs/g | 24 | 90.596 | 2.731 | 6.672 |
|  | 48 | 94.19 | 2.475 | 2.572 |
| Fuelzyme ®-LF at 25 MWUs/g and SPEZYME ® FRED at 1 LUs/g | 24 | 91.121 | 2.513 | 3.763 |
|  | 48 | 94.55 | 2.504 | 1.942 |
| Fuelzyme ®-LF at 25 MWUs/g and SPEZYME ® FRED at 0 LUs/g | 24 | 91.38 | 2.482 | 3.939 |
|  | 48 | 94.515 | 2.518 | 1.98 |

The saccharified starch was further evaluated by (1) iodine test, (2) sediment test, and (3) filtration test (as previously discussed), all of which are used to evaluate the potential of converting the saccharified starch (glucose syrup) to the high fructose syrup (HFCS or HFSS).

Only the saccharification liquor from liquefaction 1 (Blend of Fuelzyme®-LF at 25 MWUs/g and SPEZYME® FRED at 5 LUs/g) was iodine negative, while all other three treatments were blue/green when stained with iodine. The tubes were left standing for 24 and results were found still similar The results from sediment test of the saccharification liquor shows that the blend of Fuelzyme®-LF at 25 MWUs/g and SPEZYME® FRED at 5 LUs/g had lowest (<3%) sediments. Sediments for Fuelzyme®-LF at 25 MWUs/g with no SPEZYME® FRED were the highest at 15%. Higher sediments are unacceptable as it may plug up the filtration and reduce the output in sweeteners applications.

TABLE 3C

The blue saccharide, sediment, filtration and glucose results for the saccharification liquor from Fuelzyme ®-LF and SPEZYME ® FRED liquefact.

| Enzyme Treatment | Sediment % | Filter g/ 15 min | Iodine Color |
|---|---|---|---|
| Fuelzyme ®-LF at 25 MWUs/g and SPEZYME ® FRED at 5 LUs/g | <3 | 87.71 | Neg/ yellow |
| Fuelzyme ®-LF at 25 MWUs/g and SPEZYME ® FRED at 2.5 LUs/g | 3 | 90.7 | Greenish |
| Fuelzyme ®-LF at 25 MWUs/g and SPEZYME ® FRED at 1 LUs/g | 6 | 21.14 | Blue |
| Fuelzyme ®-LF at 25 MWUs/g and SPEZYME ® FRED at 0 LUs/g | 15 | 11.22 | Blue |

SEQUENCE LISTING

SEQ ID NO: 1: DNA sequence of Fuelzyme LF (AF504065; SEQ ID
NO: 1 of U.S. Pat. No. 7,273,740)
```
   1 ATGGCCAAGT ACTCCGAGCT GGAAAAGGGC GGGGTCATAA TGCAGGCGTT
  51 CTACTGGGAC GTGCCTTCAG GAGGAATATG GTGGGACACA ATACGGCAGA
 101 AGATACCGGA GTGGTACGAT GCCGGAATCT CCGCAATATG GATTCCCCCG
 151 GCGAGCAAGG GCATGGGCGG CGCCTATTCG ATGGGCTACG ACCCCTACGA
 201 CTTCTTTGAC CTCGGTGAGT ACGACCAGAA GGGAACGGTA GAGACGCGCT
 251 TTGGCTCCAA GCAGGAGCTC GTGAACATGA TAAACACCGC CCACGCCTAT
 301 GGCATGAAGG TAATAGCCGA TATAGTCATC AACCACCGCG CCGGCGGTGA
 351 CCTGGAGTGG AACCCCTTCG TGAACGACTA CACCTGGACC GACTTCTCAA
 401 AGGTCGCGTC GGGTAAATAC ACGGCCAACT ACCTCGACTT CCACCCGAAC
 451 GAGCTCCATG CGGGCGATTC CGGAACATTT GGAGGCTATC CCGACATATG
 501 CCACGACAAG AGCTGGGACC AGTACTGGCT CTGGGCCAGC CAGGAGAGCT
 551 ACGCGGCATA TCTCAGGAGC ATCGGCATCG ATGCCTGGCG CTTCGACTAC
 601 GTCAAGGGCT ATGCTCCCTG GGTCGTCAAG GACTGGCTGA ACTGGTGGGG
 650 AGGCTGGGCG GTTGGAGAGT ACTGGGACAC CAACGTCGAC GCTGTTCTCA
 701 ACTGGGCATA CTCGAGCGGT GCCAAGGTCT TTGACTTCGC CCTCTACTAC
 751 AAGATGGATG AGGCCTTTGA CAACAAAAAC ATTCCAGCGC TCGTCTCTGC
 801 CCTTCAGAAC GGCCAGACTG TTGTCTCCCG CGACCCGTTC AAGGCCGTAA
 851 CCTTTGTAGC AAACCACGAC ACCGATATAA TCTGGAACAA GTATCCAGCC
 901 TACGCGTTCA TCCTCACCTA CGAGGGCCAG CCGACAATAT TCTACCGCGA
 951 CTACGAGGAG TGGCTCAACA AGGATAAGCT CAAGAACCTC ATCTGGATAC
1001 ATGAGAACCT CGCCGGAGGA AGCACCGACA TAGTCTACTA CGATAACGAT
1051 GAACTCATCT TCGTCAGGAA CGGCTACGGG GACAAGCCGG GGCTTATACC
1101 CTACATCAAC CTAGGCTCGA GCAAGGCCGG AAGGTGGGTT TATGTGCCGA
1151 AGTTCGCGGG CGCGTGCATC CACGAGTATA CTGGTAACCT CGGAGGCTGG
1201 GTAGACAAGT ACGTCTACTC AAGCGGCTGG GTCTATCTCG AAGCTCCAGC
1251 TTACGACCCT GCCAACGGGC AGTATGGCTA CTCCGTGTGG AGCTACTGCG
1301 GGGTGGGCTG A
```

SEQ ID NO: 2: synthetic construct for alpha-amylase,
Ultra-Thin or Fuelzyme-LF (AAM48115; SEQ ID NO: 2 of U.S.
Pat. No. 7,273,740)
```
   1 MAKYSELEKG GVIMQAFYWD VPSGGIWWDT IRQKIPEWYD AGISAIWIPP
  51 ASKGMGGAYS MGYDPYDFFD LGEYDQKGTV ETRFGSKQEL VNMINTAHAY
 101 GMKVIADIVI NHRAGGDLEW NPFVNDYTWT DFSKVASGKY TANYLDFHPN
 151 ELHAGDSGTF GGYPDICHDK SWDQYWLWAS QESYAAYLRS IGIDAWRFDY
 201 VKGYAPWVVK DWLNWWGGWA VGEYWDTNVD AVLNWAYSSG AKVFDFALYY
 251 KMDEAFDNKN IPALVSALQN GQTVVSRDPF KAVTFVANHD TDIIWNKYPA
 301 YAFILTYEGQ PTIFYRDYEE WLNKDKLKNL IWIHENLAGG STDIVYYDND
 351 ELIFVRNGYG DKPGLITYIN LGSSKAGRWV YVPKFAGACI HEYIGNLGGW
 401 VDKYVYSSGW VYLEAPAYDP ANGQYGYSVW SYCGVG
```

SEQ ID NO: 3: Wild-type LAT DNA (SEQ ID NO: 3 of U.S.S.N.
12/263,804, filed Nov. 3, 2008)
```
atgaaacaac aaaaacggct ttacgcccga ttgctgacgc tgttatttgc
gctcatcttc ttgctgcctc attctgcagc ttcagcagca aatcttaatg
ggacgctgat gcagtatttt gaatggtaca tgcccaatga cggccaacat
tggaagcgtt tgcaaaacga ctcggcatat ttggctgaac acggtattac
tgccgtctgg attcccccgg catataaggg aacgagccaa gcggatgtgg
gctacggtgc ttacgacctt tatgatttag gggagtttca tcaaaaaggg
acggttcgga caaagtacgg cacaaaagga gagctgcaat ctgcgatcaa
aagtcttcat tcccgcgaca ttaacgttta cggggatgtg gtcatcaacc
acaaaggcgg cgctgatgcg accgaagatg taaccgcggt tgaagtcgat
cccgctgacc gcaaccgcgt aatttcagga gaacacctaa ttaaagcctg
gacacatttt cattttccgg ggcgcggcag cacatacagc gattttaaat
ggcattggta ccattttgac ggaaccgatt gggacgagtc ccgaaagctg
aaccgcatct ataagtttca aggaaaggct tgggattggg aagtttccaa
tgaaaacggc aactatgatt atttgatgta tgccgacatc gattatgacc
atcctgatgt cgcagcagaa attaagagat ggggcacttg gtatgccaat
gaactgcaat tggacggttt ccgtcttgat gctgtcaaac acattaaatt
ttcttttttg cgggattggg ttaatcatgt cagggaaaaa acggggaagg
aaatgtttac ggtagctgaa tattggcaga atgacttggg cgcgctggaa
aactatttga caaaacaaa ttttaatcat tcagtgtttg acgtgccgct
tcattatcag ttccatgctg catcgacaca gggaggcggc tatgatatga
ggaaattgct gaacggtacg gtcgtttcca agcatccgtt gaaatcggtt
acatttgtcg ataaccatga tacacagccg gggcaatcgc ttgagtcgac
tgtccaaaca tggtttaagc cgcttgctta cgctttttatt ctcacaaggg
aatctggata ccctcaggtt ttctacgggg atatgtacgg gacgaaagga
gactcccagc gcgaaattcc tgccttgaaa cacaaaattg aaccgatctt
aaaagcgaga aaacagtatg cgtacgagc acagcatgat tatttcgacc
accatgacat tgtcggctgg acaagggaag cgacagctc ggttgcaaat
tcaggtttgg cggcattaat aacagacgga cccgtggggg caaagcgaat
gtatgtcggc cggcaaaacg ccggtgagac atggcatgac attaccggaa
accgttcgga gccggttgtc atcaattcgg aaggctgggg agagtttcac
gtaaacggcg ggtcggttc aatttatgtt caaaga
```

SEQUENCE LISTING

SEQ ID NO: 4: Wild-type LAT polypeptide (SEQ ID NO: 4
of U.S.S.N. 12/263,804, filed Nov. 3, 2008)
ANLNGTLMQY FEWYMPNDGQ HWKRLQNDSA YLAEHGITAV WIPPAYKGTS
QADVGYGAYD LYDLGEFHQK GTVRTKYGTK GELQSAIKSL HSRDINVYGD
VVINHKGGAD ATEDVTAVEV DPADRNRVIS GEHLIKAWTH FHFPGRGSTY
SDFKWKWYHF DGTDWDESRK LNRIYKFQGK AWDWEVSNEN GNYDYLMYAD
IDYDHPDVAA EIKRWGTWYA NELQLDGFRL DAVKHIKFSF LRDWVNHVRE
KTGKEMFTVA EYWQNDLGAL ENYLNKTNFN HSVFDVPLHY QPHAASTQGG
GYDMRKLLNG TVVSKHPLKS VTFVDNHDIQ PGQSLESTVQ TWFKPLAYAF
ILTRESGYPQ VFYGDMYGTK GDSQREIPAL KHKIEPILKA RKQYAYGAQK
DYFDHHDIVG WTREGDSSVA NSGLAALITD GPGGAKRMYV GRQNAGETWH
DITGNRSEPV VINSEGWGEF HVNGGSVSIY VQR SEQ ID NO: 5: DNA sequence of FRED
AGCTTGAAGAAGTGAAGAAGCAGAGAGGCTATTGAATAAATGAGTAGAAAGCGCCATATCGG
CGCTTTTCTTTTGGAAGAAAATATAGGGAAAATGGTACTTGTTAAAAATTCGGAATATTTAT
ACAACATCATATGTTTCACATTGAAAGGGGAGGAGAATCATGAAACAACAAAAACGGCTTTA
CGCCCGATTGCTGACGCTGTTATTTGCGCTCATCTTCTTGCTGCCTCATTCTGCAGCAGCGG
CGGCAAATCTTAATGGGACGCTGATGCAGTATTTTGAATGGTACATGCCCAATGACGGCCAA
CATTGGAAGCGTTTGCAAAACGACTCGGCATATTTGGCTGAACACGGTATTACTGCCGTCTG
GATTCCCCCGGCATATAAGGGAACGAGCCAAGCGGATGTGGGCTACGGTGCTTACGACCTTT
ATGATTTAGGGGAGTTTCATCAAAAAGGGACGGTTCGGACAAAGTACGGCACAAAAGGAGAG
CTGCAATCTGCGATCAAAAGTCTTCATTCCCGCGACATTAACGTTTACGGGGATGTGGTCAT
CAACCACAAAGGCGGCGCTGATGCGACCGAAGATGTAACCGCGGTTGAAGTCGATCCCGCTG
ACCGCAACCGCGTAATTTCAGGAGAACACCTAATTAAAGCCTGGACACATTTTCATTTTCCG
GGGCGCGGCAGCACATACAGCGATTTTAAATGGCATTGGTACCATTTTGACGGAACCGATTG
GGACGAGTCCCGAAAGCTGAACCGCATCTATAAGTTTCAAGGAAAGGCTTGGGATTGGGAAG
TTTCCAATGAAAACGGCAACTATGATTATTTGATGTATGCCGACATCGATTATGACCATCCT
GATGTCGCAGCAGAAATTAAGAGATGGGGCACTTGGTATGCCAATGAACTGCAATTGGACGG
TTTCCGTCTTGATGCTGTCAAACACATTAAATTTTCTTTTTTGCGGGATTGGGTTAATCATG
TCAGGGAAAAAACGGGGAAGGAAATGTTTACGGTAGCTGAATATTGGCAGAATGACTTGGGC
GCGCTGGAAAACTATTTGAACAAAACAAATTTTAATCATTCAGTGTTTGACGTGCCGCTTCA
TTATCAGTTCCATGCTGCATCGACACAGGGAGGCGGCTATGATATGAGGAAATTGCTGAACG
GTACGGTCGTTTCCAAGCATCCGTTGAAATCGGTTACATTTGTCGATAACCATGATACACAG
CCGGGGCAATCGCTTGAGTCGACTGTCCAAACATGGTTTAAGCCGCTTGCTTACGCTTTTAT
TCTCACAAGGGAATCTGGATACCCTCAGGTTTTCTACGGGGATATGTACGGGACGAAAGGAG
ACTCCCAGCGCGAAATTCCTGCCTTGAAACACAAATTGAACCGATCTTAAAAGCGAGAAAA
CAGTATGCGTACGGAGCACAGCATGATTATTTCGACCACCATGACATTGTCGGCTGGACAAG
GGAAGGCGACAGCTCGGTTGCAAATTCAGGTTTGGCGGCATTAATAACAGACGGACCCGGTG
GGGCAAAGCGAATGTATGTCGGCCGGCAAAACGCCGGTGAGACATGGCATGACATTACCGGA
AACCGTTCGGAGCCGGTTGTCATCAATTCGGAAGGCTGGGGAGAGTTTCACGTAAACGGCGG
GTCGGTTTCAATTTATGTTCAAAGATAGAAGAGCAGAGAGGACGGATTTCCTGAAGGAAATC
CGTTTTTTTATTTTGCCCGTCTTATAAATTTCTTTGATTACATTTTATAATTAATTTTAACA
AAGTGTCATCAGCCCTCAGGAAGGACTTGCTGACAGTTTGAATCGCATAGGTAAGGCGGGGA
TGAAATGGCAACGTTATCTGATGTAGCAAAGAAAGCAAATGTGTCGAAAATGACGGTATCGC
GGGTGATCAATCATCCTGAGACTGTGACGGATGAATTGAAAAAGCT SEQ ID NO: 6: SPEZYME ®FRED alpha-amylase amino acid sequence.
  1 MKQQKRLYAR LLTLLLFALIF LLPHSAAAAA NLNGTLMQYF EWYTPNDGQH
 51 WKRLQNDSAY LAEHGITAVW IPPAYKGTSQ ADVGYGAYDL YDLGEFHQKG
101 TVRTKYGTKG ELQSAIKSLH SRDINVYGDV VINHKGGADA TEDVTAVEVD
151 PADRNRVISG EYLIKAWTHF HFPGRGSTYS DFKWKWYHPD GTDWDESRKL
201 NRIYKFQGKA WDWEVSSENG NYDYLMYADI DYDHPDVVAE IKRWGTWYAN
251 ELQLDGFRLD AVKHIKFSFL RDWVNHVREK TGKEMFTVAE YWQNDLGALE
301 NYLNKINFNH SVFDVPLHYQ FHAASTQGGG YDMRKLLNGT VVSKHPLKSV
351 TFVDNHDTQP GQSLESTVQT WFKPLAYAFI LTRESGYPQV FYGDMYGTKG
401 DSQREIPALK HKIEPILKAR KQYAYGAQHD YFDHHDIVGW TREGDSSVAN
451 SGLAALITDG PGGAKRMYVG RQNAGETWHD ITGNRSEPVV INSEGWGEFH
501 VNGGSVSIYV QR

What is claimed is:

1. An enzyme blend for processing a starch comprising a low pH, thermostable alpha-amylase and a *Bacillus licheniformis* alpha-amylase, wherein the low pH, thermostable alpha-amylase has an amino acid sequence that is at least about 85% identical to SEQ ID NO: 2, wherein the *B. licheniformis* alpha-amylase has an amino acid sequence that is at least about 90% identical to SEQ ID NO: 6, and wherein the enzyme blend contains at least about 0.5 to about 5.0 Liquefon Units (LUs) of the *B. licheniformis* alpha-amylase for every 5.0 Modified Wohlgemuth Units (MWUs) of the low pH, thermostable alpha-amylase.

2. The enzyme blend of claim 1, wherein the *B. licheniformis* alpha-amylase is a variant having one or more altered properties compared to the *B. licheniformis* alpha-amylase having an amino acid sequence of SEQ ID NO: 6, wherein the one or more altered properties include: substrate specificity, substrate binding, substrate cleavage pattern, thermal stability, pH activity profile, pH stability profile, stability towards oxidation, stability at lower levers of calcium ion (Ca2+), specific activity, or any combination thereof.

3. The enzyme blend of claim 1, wherein the low pH, thermostable alpha-amylase comprises an amino acid sequence of SEQ ID NO: 2.

4. The enzyme blend of claim 1, wherein the low pH, thermostable alpha-amylase consists of an amino acid sequence of SEQ ID NO: 2.

5. The enzyme blend of claim 1 containing at least about 1.0 Liquefon Unit (LU) of the *B. licheniformis* alpha-amylase for every 5.0 Modified Wohlgemuth Units (MWUs) of the low pH, thermostable alpha-amylase per gram dry solid (/g DS) starch.

6. The enzyme blend of claim 1, wherein at least one alpha-amylase is purified.

7. The enzyme blend of claim 1 further comprising a phytase.

8. A method of processing a starch or grain, comprising contacting the enzyme blend of claim 1 to a starch and liquefying the starch to form a liquefact.

9. The method of claim 8, wherein liquefying the starch is performed at about 80° C. to about 95° C.

10. The method of claim 8, wherein liquefying the starch is performed at about pH 5.0 to about pH 6.0.

11. The method of claim 8, wherein the liquefact has a DE value of at least about 10 within about 90-100 minutes.

12. The method of claim 8 further comprising saccharifying the liquefact to generate a saccharide syrup.

13. The method of claim 12, wherein the saccharide syrup contains at least about 90% glucose.

14. The method of claim 12, wherein the saccharide syrup contains less than about 1.5% v/v sediment.

15. The method of claim 12, wherein the saccharide syrup has a filtration rate at least about 67 g/15 minutes.

16. The method of claim 12 further comprising producing a high fructose syrup from the saccharide syrup.

17. The method of claim 16, wherein the high fructose syrup is produced by contacting a glucose isomerase to the saccharide syrup.

18. The method of claim 17, wherein the glucose isomerase is immobilized on a solid support.

19. A method of processing a starch or grain, comprising contacting a low pH, thermostable alpha-amylase and a *Bacillus licheniformis* alpha-amylase to a starch and liquefying the starch to form a liquefact, wherein the low pH, thermostable alpha-amylase has an amino acid sequence that is at least about 85% identical to SEQ ID NO: 2, wherein the *Bacillus licheniformis* alpha-amylase has an amino acid sequence that is at least about 90% identical to SEQ ID NO: 6, wherein the *Bacillus licheniformis* alpha-amylase is used at least about 0.5 to about 5.0 Liquefon Units (LUs) for every 5.0 Modified Wohlgemuth Units (MWUs) of the low pH, thermostable alpha-amylase per gram dry solid (/g DS) starch, and wherein the liquefact has a DE value of at least about 10 within about 90-100 minutes.

20. The method of claim 19, wherein contacting the low pH, thermostable alpha-amylase to the starch and contacting the *B. licheniformis* alpha-amylase to the starch occur simultaneously or sequentially.

21. The method of claim 19, wherein the *B. licheniformis* alpha-amylase is a variant having one or more altered properties compared to the *B. licheniformis* alpha-amylase having an amino acid sequence of SEQ ID NO: 6, and wherein the one or more altered properties include: substrate specificity, substrate binding, substrate cleavage pattern, thermal stability, pH activity profile, pH stability profile, stability towards oxidation, stability at lower levels of calcium ion (Ca2+), specific activity, or any combination thereof.

22. The method of claim 19, wherein the low pH, thermostable alpha-amylase comprises an amino acid sequence of SEQ ID NO: 2.

23. The method of claim 19, wherein the low pH, thermostable alpha-amylase consists of an amino acid sequence of SEQ ID NO: 2.

24. The method of claim 19, wherein the *B. licheniformis* alpha-amylase is used at an amount of at least about 1.0 Liquefon Unit (LU) for every 5.0 Modified Wohlgemuth Units (MWUs) of the low pH, thermostable alpha-amylase.

25. The method of claim 19, wherein at least one alpha-amylase is purified.

26. The method of claim 19 further comprising contacting a phytase to the starch.

27. The method of claim 19, wherein liquefying the starch is performed at about 80° C. to about 95° C.

28. The method of claim 19, wherein liquefying the starch is performed at about pH 5.0 to about pH 6.0.

29. The method of claim 19 further comprising saccharifying the liquefact to generate a saccharide syrup.

30. The method of claim 29, wherein the saccharide syrup contains at least about 90% glucose.

31. The method of claim 29, wherein the saccharide syrup contains less than about 1.5% v/v sediment.

32. The method of claim 19, wherein the saccharide syrup has a filtration rate at least about 67 g/15 minutes.

33. The method of claim 19 further comprising producing a high fructose syrup from the saccharide syrup.

34. The method of claim 33, wherein the high fructose syrup is produced by contacting a glucose isomerase to the saccharide syrup.

35. The method of claim 34, wherein the glucose isomerase is immobilized on a solid support.

* * * * *

SEQUENCE LISTING

<160> NUMBER OF SEQ ID NOS: 6

<210> SEQ ID NO 1
<211> LENGTH: 1311
<212> TYPE: DNA
<213> ORGANISM: Artificial Sequence
<220> FEATURE:
<223> OTHER INFORMATION: Synthetic DNA sequence of Fuelzyme LF

<400> SEQUENCE: 1

```
atggccaagt actccgagct ggaaaagggc ggggtcataa tgcaggcgtt ctactgggac      60
gtgccttcag gaggaatatg gtgggacaca atacggcaga agataccgga gtggtacgat     120
gccggaatct ccgcaatatg gattcccccg gcgagcaagg gcatgggcgg cgcctattcg     180
atgggctacg accctacga cttctttgac ctcggtgagt acgaccagaa gggaacggta     240
gagacgcgct ttggctccaa gcaggagctc gtgaacatga taaacaccgc ccacgcctat     300
ggcatgaagg taatagccga tatagtcatc aaccaccgcg ccggcggtga cctggagtgg     360
aaccccttcg tgaacgacta tacctggacc gacttctcaa aggtcgcgtc gggtaaatac     420
acggccaact acctcgactt ccacccgaac gagctccatg cgggcgattc cggaacattt     480
ggaggctatc ccgacatatg ccacgacaag agctgggacc agtactggct ctgggccagc     540
caggagagct acgcggcata tctcaggagc atcggcatcg atgcctggcg cttcgactac     600
gtcaagggct atgctccctg ggtcgtcaag gactggctga actggtgggg aggctgggcg     660
gttggagagt actgggacac caacgtcgac gctgttctca actgggcata ctcgagcggt     720
gccaaggtct ttgacttcgc cctctactac aagatggatg aggcctttga caacaaaaac     780
attccagcgc tcgtctctgc ccttcagaac ggccagactg ttgtctcccg cgacccgttc     840
aaggccgtaa ccttttgtagc aaaccacgac accgatataa tctggaacaa gtatccagcc     900
tacgcgttca tcctcaccta cgagggccag ccgacaatat tctaccgcga ctacgaggag     960
tggctcaaca aggataagct caagaacctc atctggatac atgagaacct cgccggagga    1020
agcaccgaca tagtctacta cgataacgat gaactcatct tcgtcaggaa cggctacggg    1080
gacaagccgg ggcttataac ctacatcaac ctaggctcga gcaaggccgg aaggtgggtt    1140
tatgtgccga gttcgcgggg cgcgtgcatc cacgagtata ctggtaacct cggaggctgg    1200
gtagacaagt acgtctactc aagcggctgg gtctatctcg aagctccagc ttacgaccct    1260
gccaacgggc agtatggcta ctccgtgtgg agctactgcg gggtgggctg a             1311
```

<210> SEQ ID NO 2
<211> LENGTH: 436
<212> TYPE: PRT
<213> ORGANISM: Artificial Sequence
<220> FEATURE:
<223> OTHER INFORMATION: Synthetic construct for alpha-amylase

<400> SEQUENCE: 2

Met Ala Lys Tyr Ser Glu Leu Glu Lys Gly Gly Val Ile Met Gln Ala
1               5                   10                  15

Phe Tyr Trp Asp Val Pro Ser Gly Gly Ile Trp Asp Thr Ile Arg
            20                  25                  30

Gln Lys Ile Pro Glu Trp Tyr Asp Ala Gly Ile Ser Ala Ile Trp Ile
        35                  40                  45

Pro Pro Ala Ser Lys Gly Met Gly Gly Ala Tyr Ser Met Gly Tyr Asp
    50                  55                  60

Pro Tyr Asp Phe Phe Asp Leu Gly Glu Tyr Asp Gln Lys Gly Thr Val
65                  70                  75                  80

Glu Thr Arg Phe Gly Ser Lys Gln Glu Leu Val Asn Met Ile Asn Thr
                85                  90                  95

Ala His Ala Tyr Gly Met Lys Val Ile Ala Asp Ile Val Ile Asn His
            100                 105                 110

Arg Ala Gly Gly Asp Leu Glu Trp Asn Pro Phe Val Asn Asp Tyr Thr
        115                 120                 125

```
Trp Thr Asp Phe Ser Lys Val Ala Ser Gly Lys Tyr Thr Ala Asn Tyr
    130                 135                 140

Leu Asp Phe His Pro Asn Glu Leu His Ala Gly Asp Ser Gly Thr Phe
145                 150                 155                 160

Gly Gly Tyr Pro Asp Ile Cys His Asp Lys Ser Trp Asp Gln Tyr Trp
                165                 170                 175

Leu Trp Ala Ser Gln Glu Ser Tyr Ala Ala Tyr Leu Arg Ser Ile Gly
                180                 185                 190

Ile Asp Ala Trp Arg Phe Asp Tyr Val Lys Gly Tyr Ala Pro Trp Val
            195                 200                 205

Val Lys Asp Trp Leu Asn Trp Trp Gly Gly Trp Ala Val Gly Glu Tyr
210                 215                 220

Trp Asp Thr Asn Val Asp Ala Val Leu Asn Trp Ala Tyr Ser Ser Gly
225                 230                 235                 240

Ala Lys Val Phe Asp Phe Ala Leu Tyr Tyr Lys Met Asp Glu Ala Phe
                245                 250                 255

Asp Asn Lys Asn Ile Pro Ala Leu Val Ser Ala Leu Gln Asn Gly Gln
                260                 265                 270

Thr Val Val Ser Arg Asp Pro Phe Lys Ala Val Thr Phe Val Ala Asn
            275                 280                 285

His Asp Thr Asp Ile Ile Trp Asn Lys Tyr Pro Ala Tyr Ala Phe Ile
290                 295                 300

Leu Thr Tyr Glu Gly Gln Pro Thr Ile Phe Tyr Arg Asp Tyr Glu Glu
305                 310                 315                 320

Trp Leu Asn Lys Asp Lys Leu Lys Asn Leu Ile Trp Ile His Glu Asn
                325                 330                 335

Leu Ala Gly Gly Ser Thr Asp Ile Val Tyr Tyr Asp Asn Asp Glu Leu
            340                 345                 350

Ile Phe Val Arg Asn Gly Tyr Gly Asp Lys Pro Gly Leu Ile Thr Tyr
            355                 360                 365

Ile Asn Leu Gly Ser Ser Lys Ala Gly Arg Trp Val Tyr Val Pro Lys
370                 375                 380

Phe Ala Gly Ala Cys Ile His Glu Tyr Thr Gly Asn Leu Gly Gly Trp
385                 390                 395                 400

Val Asp Lys Tyr Val Tyr Ser Ser Gly Trp Val Tyr Leu Glu Ala Pro
                405                 410                 415

Ala Tyr Asp Pro Ala Asn Gly Gln Tyr Gly Tyr Ser Val Trp Ser Tyr
            420                 425                 430

Cys Gly Val Gly
        435

<210> SEQ ID NO 3
<211> LENGTH: 1536
<212> TYPE: DNA
<213> ORGANISM: Bacillus Licheniformis
<220> FEATURE:
<221> NAME/KEY: misc_feature
<223> OTHER INFORMATION: Wild-type LAT DNA

<400> SEQUENCE: 3
atgaaacaac aaaaacggct ttacgcccga ttgctgacgc tgttatttgc gctcatcttc      60
ttgctgcctc attctgcagc ttcagcagca aatcttaatg ggacgctgat gcagtatttt     120
gaatggtaca tgcccaatga cggccaacat tggaagcgtt tgcaaaacga ctcggcatat     180
ttggctgaac acggtattac tgccgtctgg attccccggg catataaggg aacgagccaa     240
```

```
gcggatgtgg gctacggtgc ttacgacctt tatgatttag gggagtttca tcaaaaaggg    300
acggttcgga caaagtacgg cacaaaagga gagctgcaat ctgcgatcaa aagtcttcat    360
tcccgcgaca ttaacgttta cggggatgtg gtcatcaacc acaaaggcgg cgctgatgcg    420
accgaagatg taaccgcggt tgaagtcgat cccgctgacc gcaaccgcgt aatttcagga    480
gaacacctaa ttaaagcctg gacacatttt cattttccgg ggcgcggcag cacatacagc    540
gattttaaat ggcattggta ccattttgac ggaaccgatt gggacgagtc ccgaaagctg    600
aaccgcatct ataagtttca aggaaaggct tgggattggg aagtttccaa tgaaaacggc    660
aactatgatt atttgatgta tgccgacatc gattatgacc atcctgatgt cgcagcagaa    720
attaagagat ggggcacttg gtatgccaat gaactgcaat tggacggttt ccgtcttgat    780
gctgtcaaac acattaaatt ttctttttg cgggattggg ttaatcatgt cagggaaaaa    840
acggggaagg aaatgtttac ggtagctgaa tattggcaga atgacttggg cgcgctggaa    900
aactatttga caaaacaaa ttttaatcat tcagtgtttg acgtgccgct tcattatcag    960
ttccatgctg catcgacaca gggaggcggc tatgatatga ggaaattgct gaacggtacg    1020
gtcgtttcca agcatccgtt gaaatcggtt acatttgtcg ataaccatga tacacagccg    1080
gggcaatcgc ttgagtcgac tgtccaaaca tggtttaagc cgcttgctta cgcttttatt    1140
ctcacaaggg aatctggata ccctcaggtt ttctacgggg atatgtacgg gacgaaagga    1200
gactcccagc gcgaaattcc tgccttgaaa cacaaaattg aaccgatctt aaaagcgaga    1260
aaacagtatg cgtacggagc acagcatgat tatttcgacc accatgacat tgtcggctgg    1320
acaagggaag cgacagctc ggttgcaaat tcaggtttgg cggcattaat aacagacgga    1380
cccggtgggg caaagcgaat gtatgtcggc cggcaaaacg ccggtgagac atggcatgac    1440
attaccggaa accgttcgga gccggttgtc atcaattcgg aaggctgggg agagtttcac    1500
gtaaacggcg ggtcggtttc aatttatgtt caaaga                              1536
```

<210> SEQ ID NO 4
<211> LENGTH: 483
<212> TYPE: PRT
<213> ORGANISM: Bacillus Licheniformis
<220> FEATURE:
<221> NAME/KEY: misc_feature
<223> OTHER INFORMATION: Wild-type LAT polypeptide

<400> SEQUENCE: 4

```
Ala Asn Leu Asn Gly Thr Leu Met Gln Tyr Phe Glu Trp Tyr Met Pro
1               5                   10                  15

Asn Asp Gly Gln His Trp Lys Arg Leu Gln Asn Asp Ser Ala Gln Ala
                20                  25                  30

Asp Val Gly Tyr Gly Ala Tyr Asp Leu Tyr Asp Leu Gly Glu Phe His
            35                  40                  45

Gln Lys Gly Thr Val Arg Thr Lys Tyr Gly Thr Lys Val Val Ile Asn
        50                  55                  60

His Lys Gly Gly Ala Asp Ala Thr Glu Asp Val Thr Ala Val Glu Val
65                  70                  75                  80

Asp Pro Ala Asp Arg Asn Arg Val Ile Ser Ser Asp Phe Lys Trp His
                85                  90                  95

Trp Tyr His Phe Asp Gly Thr Asp Trp Asp Glu Ser Arg Lys Leu Asn
                100                 105                 110

Arg Ile Tyr Lys Phe Gln Gly Lys Ile Asp Tyr Asp His Pro Asp Val
            115                 120                 125
```

```
Ala Ala Glu Ile Lys Arg Trp Gly Thr Trp Tyr Ala Asn Glu Leu Gln
        130                 135                 140

Leu Asp Gly Phe Arg Leu Lys Thr Gly Lys Glu Met Phe Thr Val Ala
145                 150                 155                 160

Glu Tyr Trp Gln Asn Asp Leu Gly Ala Leu Glu Asn Tyr Leu Asn Lys
                165                 170                 175

Thr Asn Phe Asn Gly Tyr Asp Met Arg Lys Leu Leu Asn Gly Thr Val
            180                 185                 190

Val Ser Lys His Pro Leu Lys Ser Val Thr Phe Val Asp Asn His Asp
        195                 200                 205

Thr Gln Ile Leu Thr Arg Glu Ser Gly Tyr Pro Gln Val Phe Tyr Gly
    210                 215                 220

Asp Met Tyr Gly Thr Lys Gly Asp Ser Gln Arg Glu Ile Pro Ala Leu
225                 230                 235                 240

Asp Tyr Phe Asp His His Asp Ile Val Gly Trp Thr Arg Glu Gly Asp
                245                 250                 255

Ser Ser Val Ala Asn Ser Gly Leu Ala Ala Leu Ile Thr Asp Asp Ile
            260                 265                 270

Thr Gly Asn Arg Ser Glu Pro Val Val Ile Asn Ser Glu Gly Trp Gly
        275                 280                 285

Glu Phe His Val Asn Gly Gly Ser Val Ser Ile Tyr Tyr Leu Ala Glu
    290                 295                 300

His Gly Ile Thr Ala Val Trp Ile Pro Pro Ala Tyr Lys Gly Thr Ser
305                 310                 315                 320

Gly Glu Leu Gln Ser Ala Ile Lys Ser Leu His Ser Arg Asp Ile Asn
                325                 330                 335

Val Tyr Gly Asp Gly Glu His Leu Ile Lys Ala Trp Thr His Phe His
            340                 345                 350

Phe Pro Gly Arg Gly Ser Thr Tyr Ala Trp Asp Trp Glu Val Ser Asn
        355                 360                 365

Glu Asn Gly Asn Tyr Asp Tyr Leu Met Tyr Ala Asp Asp Ala Val Lys
    370                 375                 380

His Ile Lys Phe Ser Phe Leu Arg Asp Trp Val Asn His Val Arg Glu
385                 390                 395                 400

His Ser Val Phe Asp Val Pro Leu His Tyr Gln Phe His Ala Ala Ser
                405                 410                 415

Thr Gln Gly Gly Pro Gly Gln Ser Leu Glu Ser Thr Val Gln Thr Trp
            420                 425                 430

Phe Lys Pro Leu Ala Tyr Ala Phe Lys His Lys Ile Glu Pro Ile Leu
        435                 440                 445

Lys Ala Arg Lys Gln Tyr Ala Tyr Gly Ala Gln His Gly Pro Gly Gly
    450                 455                 460

Ala Lys Arg Met Tyr Val Gly Arg Gln Asn Ala Gly Glu Thr Trp His
465                 470                 475                 480

Val Gln Arg

<210> SEQ ID NO 5
<211> LENGTH: 1968
<212> TYPE: DNA
<213> ORGANISM: Bacillus Licheniformis
<220> FEATURE:
<221> NAME/KEY: misc_feature
<223> OTHER INFORMATION: DNA sequence of FRED

<400> SEQUENCE: 5
```

-continued

| | |
|---|---|
| agcttgaaga agtgaagaag cagagaggct attgaataaa tgagtagaaa gcgccatatc | 60 |
| ggcgcttttc ttttggaaga aaatataggg aaaatggtac ttgttaaaaa ttcggaatat | 120 |
| ttatacaaca tcatatgttt cacattgaaa ggggaggaga atcatgaaac aacaaaaacg | 180 |
| gctttacgcc cgattgctga cgctgttatt tgcgctcatc ttcttgctgc ctcattctgc | 240 |
| agcagcggcg gcaaatctta atgggacgct gatgcagtat tttgaatggt acatgcccaa | 300 |
| tgacggccaa cattggaagc gtttgcaaaa cgactcggca tatttggctg aacacggtat | 360 |
| tactgccgtc tggattcccc cggcatataa gggaacgagc caagcggatg tgggctacgg | 420 |
| tgcttacgac ctttatgatt tagggggagtt tcatcaaaaa gggacggttc ggacaaagta | 480 |
| cggcacaaaa ggagagctgc aatctgcgat caaaagtctt cattcccgcg acattaacgt | 540 |
| ttacggggat gtggtcatca accacaaagg cggcgctgat gcgaccgaag atgtaaccgc | 600 |
| ggttgaagtc gatcccgctg accgcaaccg cgtaatttca ggagaacacc taattaaagc | 660 |
| ctggacacat tttcattttc cggggcgcgg cagcacatac agcgatttta aatggcattg | 720 |
| gtaccatttt gacggaaccg attgggacga gtcccgaaag ctgaaccgca tctataagtt | 780 |
| tcaaggaaag gcttgggatt gggaagtttc caatgaaaac ggcaactatg attatttgat | 840 |
| gtatgccgac atcgattatg accatcctga tgtcgcagca gaaattaaga gatggggcac | 900 |
| ttggtatgcc aatgaactgc aattggacgg tttccgtctt gatgctgtca aacacattaa | 960 |
| attttctttt ttgcgggatt gggttaatca tgtcaggaa aaaacgggga aggaaatgtt | 1020 |
| tacggtagct gaatattggc agaatgactt gggcgcgctg gaaaactatt tgaacaaaac | 1080 |
| aaattttaat cattcagtgt ttgacgtgcc gcttcattat cagttccatg ctgcatcgac | 1140 |
| acagggaggc ggctatgata tgaggaaatt gctgaacggt acggtcgttt ccaagcatcc | 1200 |
| gttgaaatcg gttacatttg tcgataacca tgatacacag ccggggcaat cgcttgagtc | 1260 |
| gactgtccaa acatggttta agccgcttgc ttacgctttt attctcacaa gggaatctgg | 1320 |
| ataccctcag gttttctacg gggatatgta cgggacgaaa ggagactccc agcgcgaaat | 1380 |
| tcctgccttg aaacacaaaa ttgaaccgat cttaaaagcg agaaaacagt atgcgtacgg | 1440 |
| agcacagcat gattatttcg accaccatga cattgtcggc tggacaaggg aaggcgacag | 1500 |
| ctcggttgca aattcaggtt tggcggcatt aataacagac ggacccggtg gggcaaagcg | 1560 |
| aatgtatgtc ggccggcaaa acgccggtga gacatggcat gacattaccg aaaaccgttc | 1620 |
| ggagccggtt gtcatcaatt cggaaggctg gggagagttt cacgtaaacg gcgggtcggt | 1680 |
| ttcaatttat gttcaaagat agaagagcag agaggacgga tttcctgaag gaaatccgtt | 1740 |
| tttttatttt gcccgtctta taaatttctt tgattacatt ttataattaa ttttaacaaa | 1800 |
| gtgtcatcag ccctcaggaa ggacttgctg acagtttgaa tcgcataggt aaggcgggga | 1860 |
| tgaaatggca acgttatctg atgtagcaaa gaaagcaaat gtgtcgaaaa tgacggtatc | 1920 |
| gcgggtgatc aatcatcctg agactgtgac ggatgaattg aaaaagct | 1968 |

<210> SEQ ID NO 6
<211> LENGTH: 512
<212> TYPE: PRT
<213> ORGANISM: Bacillus licheniformis
<220> FEATURE:
<221> NAME/KEY: misc_feature
<223> OTHER INFORMATION: SPEZYME FRED alpha-amylase amino acid sequence

<400> SEQUENCE: 6

Met Lys Gln Gln Lys Arg Leu Tyr Ala Arg Leu Leu Thr Leu Leu Phe
1               5                   10                  15

```
Ala Leu Ile Phe Leu Leu Pro His Ser Ala Ala Ala Asn Leu
            20                  25              30

Asn Gly Thr Leu Met Gln Tyr Phe Glu Trp Tyr Thr Pro Asn Asp Gly
        35                  40                  45

Gln His Trp Lys Arg Leu Gln Asn Asp Ser Ala Tyr Leu Ala Glu His
50                  55                  60

Gly Ile Thr Ala Val Trp Ile Pro Pro Ala Tyr Lys Gly Thr Ser Gln
65                  70                  75                  80

Ala Asp Val Gly Tyr Gly Ala Tyr Asp Leu Tyr Asp Leu Gly Glu Phe
                85                  90                  95

His Gln Lys Gly Thr Val Arg Thr Lys Tyr Gly Thr Lys Gly Glu Leu
            100                 105                 110

Gln Ser Ala Ile Lys Ser Leu His Ser Arg Asp Ile Asn Val Tyr Gly
        115                 120                 125

Asp Val Val Ile Asn His Lys Gly Gly Ala Asp Ala Thr Glu Asp Val
    130                 135                 140

Thr Ala Val Glu Val Asp Pro Ala Asp Arg Asn Arg Val Ile Ser Gly
145                 150                 155                 160

Glu Tyr Leu Ile Lys Ala Trp Thr His Phe His Phe Pro Gly Arg Gly
                165                 170                 175

Ser Thr Tyr Ser Asp Phe Lys Trp His Trp Tyr His Phe Asp Gly Thr
            180                 185                 190

Asp Trp Asp Glu Ser Arg Lys Leu Asn Arg Ile Tyr Lys Phe Gln Gly
        195                 200                 205

Lys Ala Trp Asp Trp Glu Val Ser Ser Glu Asn Gly Asn Tyr Asp Tyr
210                 215                 220

Leu Met Tyr Ala Asp Ile Asp Tyr Asp His Pro Asp Val Val Ala Glu
225                 230                 235                 240

Ile Lys Arg Trp Gly Thr Trp Tyr Ala Asn Glu Leu Gln Leu Asp Gly
                245                 250                 255

Phe Arg Leu Asp Ala Val Lys His Ile Lys Phe Ser Phe Leu Arg Asp
            260                 265                 270

Trp Val Asn His Val Arg Glu Lys Thr Gly Lys Glu Met Phe Thr Val
        275                 280                 285

Ala Glu Tyr Trp Gln Asn Asp Leu Gly Ala Leu Glu Asn Tyr Leu Asn
290                 295                 300

Lys Thr Asn Phe Asn His Ser Val Phe Asp Val Pro Leu His Tyr Gln
305                 310                 315                 320

Phe His Ala Ala Ser Thr Gln Gly Gly Gly Tyr Asp Met Arg Lys Leu
                325                 330                 335

Leu Asn Gly Thr Val Val Ser Lys His Pro Leu Lys Ser Val Thr Phe
            340                 345                 350

Val Asp Asn His Asp Thr Gln Pro Gly Gln Ser Leu Glu Ser Thr Val
        355                 360                 365

Gln Thr Trp Phe Lys Pro Leu Ala Tyr Ala Phe Ile Leu Thr Arg Glu
370                 375                 380

Ser Gly Tyr Pro Gln Val Phe Tyr Gly Asp Met Tyr Gly Thr Lys Gly
385                 390                 395                 400

Asp Ser Gln Arg Glu Ile Pro Ala Leu Lys His Lys Ile Glu Pro Ile
                405                 410                 415

Leu Lys Ala Arg Lys Gln Tyr Ala Tyr Gly Ala Gln His Asp Tyr Phe
            420                 425                 430
```

-continued

```
Asp His His Asp Ile Val Gly Trp Thr Arg Glu Gly Asp Ser Ser Val
        435                 440                 445

Ala Asn Ser Gly Leu Ala Ala Leu Ile Thr Asp Gly Pro Gly Gly Ala
    450                 455                 460

Lys Arg Met Tyr Val Gly Arg Gln Asn Ala Gly Glu Thr Trp His Asp
465                 470                 475                 480

Ile Thr Gly Asn Arg Ser Glu Pro Val Val Ile Asn Ser Glu Gly Trp
                485                 490                 495

Gly Glu Phe His Val Asn Gly Gly Ser Val Ser Ile Tyr Val Gln Arg
            500                 505                 510
```